(12) United States Patent
Ishige et al.

(10) Patent No.: US 8,128,796 B2
(45) Date of Patent: Mar. 6, 2012

(54) ANALYZER

(75) Inventors: Yu Ishige, Tokyo (JP); Masao Kamahori, Kokubunji (JP)

(73) Assignee: Hitachi, Limited, Tokyo (JP)

( * ) Notice: Subject to any disclaimer, the term of this patent is extended or adjusted under 35 U.S.C. 154(b) by 928 days.

(21) Appl. No.: 12/155,919

(22) Filed: Jun. 11, 2008

(65) Prior Publication Data
US 2008/0314746 A1 Dec. 25, 2008

(30) Foreign Application Priority Data
Jun. 22, 2007 (JP) ................................ 2007-165117

(51) Int. Cl.
G01N 33/487 (2006.01)
(52) U.S. Cl. .................. 204/403.01; 435/6.1; 205/777.5
(58) Field of Classification Search ...... 204/403.01–403.15; 435/6; 205/777.5; 257/253
See application file for complete search history.

(56) References Cited

U.S. PATENT DOCUMENTS

| | | | |
|---|---|---|---|
| 7,960,113 B2 * | 6/2011 | Ishige et al. | 435/6.11 |
| 2004/0121354 A1 * | 6/2004 | Yazawa et al. | 435/6 |

FOREIGN PATENT DOCUMENTS

| | | | |
|---|---|---|---|
| EP | 1669748 A1 | * | 6/2006 |
| JP | 57082769 A | | 11/1980 |
| JP | 9-500727 | | 7/1994 |
| JP | 2008233050 A | * | 10/2008 |
| WO | WO 95/03543 | | 7/1994 |

OTHER PUBLICATIONS

Margulies, Marcel, et al, Genome Sequencing in Microfabricated High-density Picolitre Reactors, Nature, 2005, pp. 1-5.*
Sakata, Toshiya, and Yuji Miyahara. "DNA Sequencing Based on Intrinsic Molecular Charges." Angewandte Chemie International Edition 45.14 (2006): 2225-228.*
Katherine A. Erickson et al.; "Evaluation of a Novel Point-of-Care System, the i-STAT Portable Clinical Analyzer"; Clinical Chemistry, vol. 39, No. 2, pp. 283-287 (1993).

* cited by examiner

Primary Examiner — Kaj K Olsen
Assistant Examiner — Kourtney R Salzman
(74) Attorney, Agent, or Firm — Stites & Harbison, PLLC; Juan Carlos A. Marquez, Esq.

(57) ABSTRACT

It is an object of this invention to measure small amounts of a plurality of sample solutions at the same time. The small amounts of sample solutions are respectively placed on measuring electrodes, a medium is placed across the plurality of sample solutions, a liquid joint of a reference electrode is brought into contact with the medium, and a potential difference between each of the measuring electrodes and the reference electrode via the medium is measured.

20 Claims, 15 Drawing Sheets

ANALYZER

CLAIM OF PRIORITY

The present application claims priority from Japanese application JP 2007-165117 filed on Jun. 22, 2007, the content of which is hereby incorporated by reference into this application.

BACKGROUND OF THE INVENTION

1. Field of the Invention

The present invention relates to an analyzer for analyzing a biological substance and the method thereof.

2. Description of the Related Art

Recent progress in medicine is remarkable and many diseases are rapidly and appropriately diagnosed and treated. Accordingly, people can healthily live mentally and physically. In addition, implementation of a variety of medical inspections such as examination of lifestyle diseases successfully leads to early recognition and treatment. A variety of these diagnoses and inspections are conducted by a clinical analyzer primarily using blood or urine as a specimen (Japanese Patent Application Publication No. Sho 57-82769).

Clinical analyzers employs absorptiometry that analyzes substances such as sugar, proteins, lipids and enzymes in blood being a specimen by use of enzyme reactions or chemical reactions of colorimetric reagents.

In order to decrease a burden on a patient with less invasiveness (reduction of the amount of blood sample) and to lower a cost with less amount of reagent used, clinical analyzers are now further developed to use only a smaller amount of a sample solution to be measured (hereinafter, simply referred to as a sample solution) for analysis. The use of a smaller amount of a sample solution is also beneficial to the reduction of the amount of waste liquids.

However, a smaller amount of sample solution in absorbance measurement cannot be obtained simply by making the analyzer smaller accordingly. Absorbance A follows the Beer-Lambert Law expressed by:

$A = \epsilon c l$ $\epsilon$: Molar absorption coefficient
c: Specimen concentration
l: Light pathway length Because of this, when the amount of a sample solution is made small, the light pathway length l needs to be as long as in a conventional analyzer in order to obtain the same level of a change of the absorption coefficient as in the conventional analyzer. Hence, an elongated cell has to be placed in the progress direction of light for reducing the amount of a sample solution, whereby reducing the amount of sample solution simply by miniaturizing the optical system is not realistic. Moreover, when the cross section of a light beam for irradiation is made small in proportion to the reduction of the amount of sample solution, the intensity of a signal obtained by a light detector is decreased, thereby creating the problem of decreasing in measurement precision.

As a measuring device using electrochemical detection, known is an enzyme sensor that uses amperometry as a measuring principle. A glucose sensor, one example of enzyme sensors, uses a hydrogen peroxide electrode. Glucose in blood being a specimen is reacted with dissolved oxygen by the action of glucose oxidase to generate hydrogen peroxide. The generated hydrogen peroxide is converted into electric current by the reaction $H_2O_2 \rightarrow 2H^+ + O_2 + 2e^-$ on the hydrogen peroxide electrode, so that the concentration of the glucose is determined by the measurement of the current. In addition, portable clinical analyzers capable of measuring a multinominal substance utilizing the above principle include i-Stat (Clin. Chem. 39/2 (1993) 283-287). In amperometry, the intensity of a signal depends on the area of an electrode, so that making the amount of a reaction solution small is difficult as in absorbance measurement. For example, the amount of electric current generated by redox reaction on the electrode surface of a redox compound is proportional to the product of the concentration of the redox compound and the area of the electrode.

On the other hand, also available is a portable clinical analyzer that measures glucose with use of potentiometry (Japanese Patent Translation Publication No. Hei 9-500727). This sensor includes a working electrode made from gold, platinum or the like and a reference electrode, and uses a sample solution containing an enzyme and a redox compound. Additionally, the working electrode and the reference electrode are connected to a device for measuring a potential difference. When an analyte is added into a sample solution, the analyte is oxidized by enzyme reaction and at the same time the redox compound in an oxidation state is reduced. The potential difference between the working and reference electrodes generated at the time follows the next Nernst equation.

$$E = E^0 + \frac{RT}{nF}\ln(C_{ox}/C_{red})$$

E: Surface potential of working electrode
$E^0$: Standard potential of redox compound
R: Universal gas constant
T: Absolute temperature
n: Difference of charge of oxidation and reduction types of redox compound
F: Faraday constant
$C_{ox}$: Concentration of oxidation type of redox compound
$C_{red}$: Concentration of reduction type of redox compound The above equation shows that the potential difference between the working and reference electrodes does not depend on the electrode area. As a result, in a portable clinical analyzer using potentiometry, the intensity of a signal does not decrease even if the amount of sample solution is made small.

SUMMARY OF THE INVENTION

Potentiometry in which the intensity of a signal does not depend on the amount of solution and the area of the electrode is suitable for making the amount of sample solution small. However, fabrication of an apparatus that can measure a plurality of samples and attributes at the same time using potentiometry causes a new problem. Because of a need for a reference electrode as a standard potential in potentiometry, the number of reference electrodes needs to be equal to the number of samples. As a large number of reference electrodes are required, not only the cost of the device is increased, but an error of potential difference will occur due to a variation among reference electrodes.

Furthermore, in the measurement of a small amount of sample solution, the reference electrode needs to be miniaturized. In that case, it is difficult to miniaturize a reference electrode having an internal liquid usually used while maintaining its stability and life. In the present situations, quasi-reference electrodes such as a silver-silver chloride electrode having no internal liquid are employed, so that there are problems in stability and life.

For solving the above problems, the present invention carries out potentiometry using a liquid immiscible with water as a medium. A liquid containing an organic salt and being immiscible with water or an organic salt itself is arranged across a plurality of vessels, and a reference electrode having an internal liquid is arranged so that the internal liquid of the reference electrode makes contact with the above medium. Desirably, the amount of internal liquid of a reference electrode is made larger than the amount of each sample solution.

Arrangement of a liquid immiscible with water as a medium across a plurality of cells enables suppression of mixture of samples and also measurement of interfacial potentials of a plurality of electrodes with use of a reference electrode having a single internal liquid. Due to the use of a single reference electrode, the variation among reference electrodes which might occur when a plurality of reference electrodes are used does not occur as a problem in this case. The use of a reference electrode having an internal liquid does not create the problems of stability and life, which the conventional quasi-electrodes have. Desirably, if the amount of the internal liquid of a reference electrode is made larger than the amount of each sample solution, a standard potential can be only less influenced when a minute leakage current is generated. When a vessel is miniaturized for the measurement of a small amount of sample, a reference electrode having an internal liquid with a volume too large to be contained in the vessel can be used. Accordingly, a stable standard potential can be obtained. Making one vessel serve as a reference electrode having an internal liquid further enables the miniaturization of a device. Inclusion of an organic salt in a medium suppresses bias in the potential distribution within the medium, thereby reducing a measurement error attributable to the bias in the potential distribution within the medium.

DESCRIPTION OF THE PREFERRED EMBODIMENTS

Hereinafter, embodiments of the present invention will be described with reference to the drawings.

Figure 1:
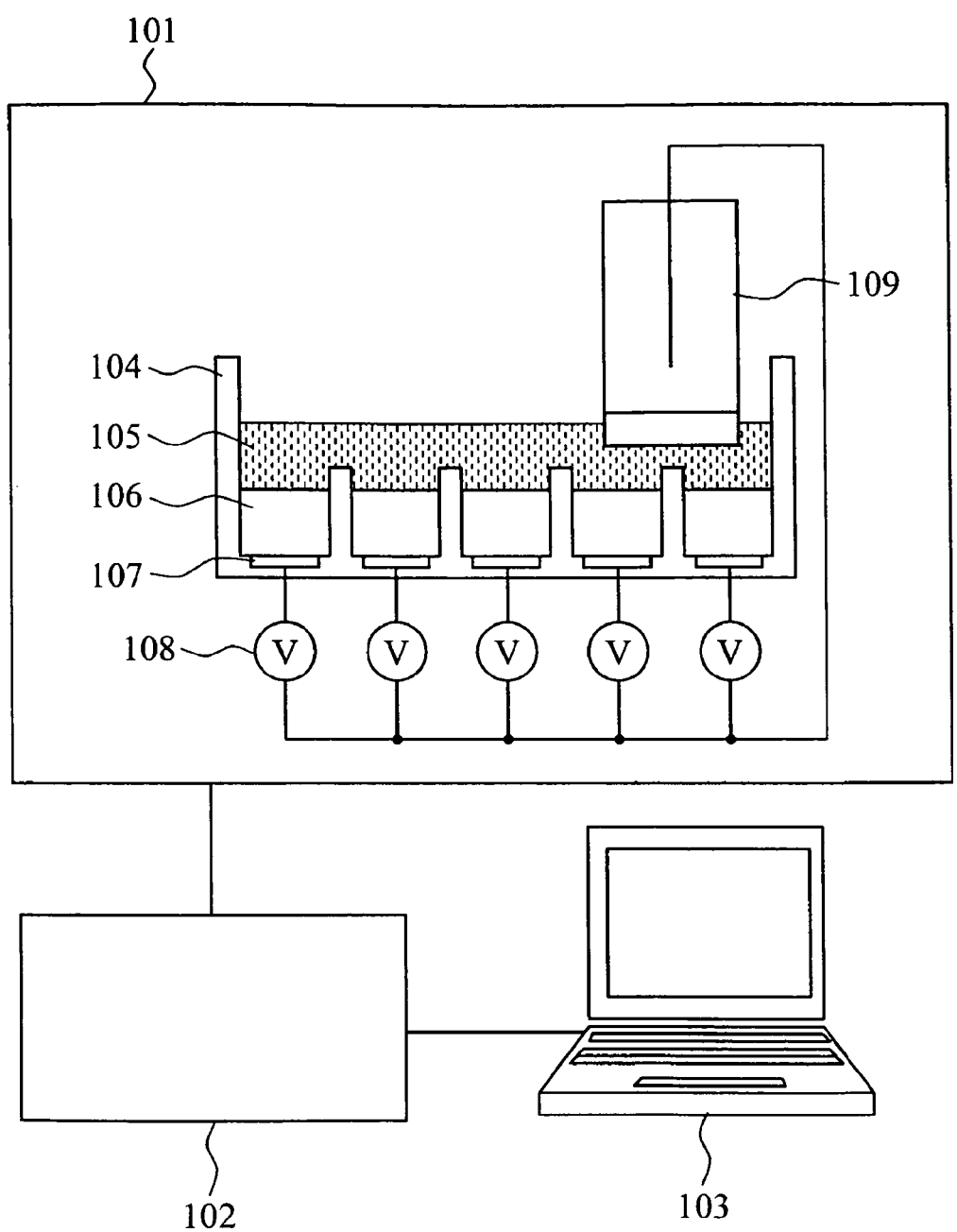
FIG. 1 is a block diagram indicating one example of an analyzer for analyzing a small amount of liquid according to present invention.

FIG. 1 is a block diagram indicating one example of a small analyzer according to the present invention. An analyzer of the present invention includes a measuring section 101, a signal processing circuit 102, and a data processing device 103. The measuring section 101 includes a measuring container 104, a medium 105, a sample solution 106, an electrode 107, a voltmeter 108, and a reference electrode 109. The measuring container 104 is partitioned into a plurality of vessels by partitioning walls. One electrode 107 is arranged in each vessel; one voltmeter 108 is connected to each of the electrodes 107; and the other end of the voltmeter 108 is communicated with the reference electrode 109. The sample solution 106 is present in each vessel, and the medium 105 is present across the plurality of the vessels. The medium 105 makes contact with a plurality of sample solutions 106 and the reference electrode 109.

One example of measuring procedures will be depicted. First, the sample solution 106 is poured into each vessel. At this time, the sample solution 106 is poured so as not to overflow from a vessel. Next, the medium 105 is poured into the measuring container 104 across the plurality of the vessels. When the specific gravity of the medium 105 is larger than that of the sample solution 106, the medium 105 is carefully poured so as not to enter into the lower part of the sample solution 106. Then, the reference electrode 109 is arranged such that a liquid junction makes contact with the medium 105. Finally, a potential indicated by each of the voltmeters 108 is read out.

The sample solution 106 may be poured so as to almost overflow from each vessel in order to make the sample solution 106 contact the medium 105 readily. In addition, after the medium 105 is poured thereinto, each of the sample solutions 106 is poured into each vessel in some cases as well. Different solutions such as a sample and a reagent may be poured into one vessel so that those different solutions react with each other in the vessel.

A liquid immiscible with water is used as the medium 105. Use of a liquid immiscible with water prevents the sample solutions 106 in a plurality of vessels from mixing with each other and makes it possible to read interfacial potentials between the electrodes 107 arranged within the plurality of vessels and the sample solutions 106. For example, although the interfacial potentials between the electrodes 107 arranged in a plurality of vessels and the sample solutions 106 can be read also by use of a liquid miscible with water as the medium 105, there are fears that the liquid would mix with each of the sample solutions 106 and further that each of the sample solutions 106 would mix with each other.

The measurement of the potential difference between the reference electrode 109 and the electrode 107 arranged in each vessel via the medium 105 enables a reference electrode having a cross section larger than the cross section of each vessel to be employed. The measurement of the potential difference between the reference electrode 109 and the electrode 107 arranged within each vessel without using the medium 105 may be done, for example, by arrangement of a reference electrode within each vessel. However, in this case, the cross section of each vessel must have a size that can embrace the cross section of the reference potential. Accordingly, if an interfacial potential between the electrode 107 arranged within each vessel and the sample solution 106 is read out using a smaller amount of the sample solution 106, the cross section of a reference electrode needs to be made small. A small reference electrode has disadvantages as compared with a large reference electrode in terms of the clogging of a liquid junction, stability of the potential and life. In an actual case, a quasi-electrode such as a silver-silver chloride electrode not having an internal liquid is frequently used as a small reference electrode; however, this electrode is more disadvantageous in stability and life.

If the interfacial potential between the electrode 107 arranged within each vessel and the sample solution 106 is read out via the medium 105, reference electrodes the number of which is smaller than that of the vessels can be used. When the interfacial potential between the electrode 107 arranged within each vessel and the sample solution 106 is read out without using the medium 105, for example, it is considered that a reference electrode is arranged within each vessel. However, in this case, reference electrodes the number of which is equal to that of the vessels are needed. Thus, the apparatus becomes costly, and, in some cases, the variation of the potentials between each of the reference electrodes poses a problem. Alternatively, it is considered that one reference electrode is alternately arranged in each vessel and that the interfacial potential between the electrode 107 arranged within each vessel and the sample solution 106 is read out one by one. In this case, the above mentioned cost and the variation of the potential between each of the reference electrodes do not create a problem, while the reference electrodes need to be washed for every potential measurement, which is time-consuming, in order to prevent mixing of each of the sample solutions 106, and the case needs time for measurement due to every potential difference being read out one by one, as compared with the case of reading a plurality of potential differences at one time.

Placing the medium 105 so as to cover the sample solution 106 renders it possible to prevent the evaporation of the sample solution 106. A small amount of sample solution renders the effect of evaporation of a sample solution remarkable. At the time, the evaporation of a sample solution can be restrained with the sample solution covered with some material immiscible with the sample solution, and the placement of the medium 105 like the present example enables the restraint of the evaporation and the measurement of the potential to be simultaneously performed.

The medium 105 desirably contains an organic salt. Alternatively, a liquid organic salt is desirably used. When the medium 105 has insulating properties, a potential gradient may be generated within the medium. In this case, the potentials within media near each of the vessels are not equal to each other, so it is difficult to more precisely measure the interfacial potential between the electrode 107 arranged in each vessel and the sample solution 106. The value $V_n$ of each voltmeter 108 communicated with the electrode 107 arranged within each vessel n is given by:

$$V_n = V_{Ref} + \Phi_{Ref} + V_{Grad,n} + \Phi_{pho,n} + \Phi_n$$

wherein $V_{Ref}$: Interfacial potential of the reference electrode 109, $\Phi_{Ref}$: Interfacial potential between an internal liquid of the reference electrode 109 and the medium 105, $V_{Grad,n}$: Potential gradient between the vicinities of the reference electrode 109 and each vessel n, within the medium 105, $\Phi_{pho,n}$: Interfacial potential between the medium 105 and each of the sample solutions 106 within each of the vessels n, and $\Phi_n$: Interfacial potential between the electrode 107 arranged within each of the vessels n and the sample solution 106.

On the basis of the above equation, $\Phi_n$ can be determined from $V_n$. Here, $V_{Ref}$ and $\Phi_{Ref}$ do not depend on the vessel n. Assuming that $\Phi_{pho,n}$ is not largely changed between each sample solution, $\Phi_n$ can be determined from $V_n$ if $V_{Grad,n}$ is equal to 0. However, if $V_{Grad,n}$ is present, a precise $\Phi_n$ cannot be determined from $V_n$. If an organic salt dissolves in the medium 105, the organic salt becomes a supporting electrolyte, whereby $V_{Grad,n}$ can be decreased, thereby being capable of more precisely determining $\Phi_n$ from $V_n$. Furthermore, the medium 105 or the sample solution 106 desirably contains a salt that can dissolve in both the liquids. The presence of such a salt enables $\Phi_{pho,n}$ to be decrease, thereby being able to more precisely obtain $\Phi_n$ from $V_n$.

The reference electrodes 109 that can be used include, in addition to a silver-silver chloride electrode having an internal liquid, a standard hydrogen electrode, a saturated calomel electrode, a mercury-mercurous sulfate electrode and a mercurous oxide electrode, a reference electrode that uses as a standard potential an electrode reaction of a reversible redox system like ferrocene/ferrocenium ion, or ferricyanide/ferrocyanide. The electrodes 107 that can be used include noble metals such as gold, silver, copper and platinum, the metals above modified with an alkanethiol single molecular film, and further electrodes modified with an ion-sensitive membrane, and the like. The mediums 105 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

Figure 2:
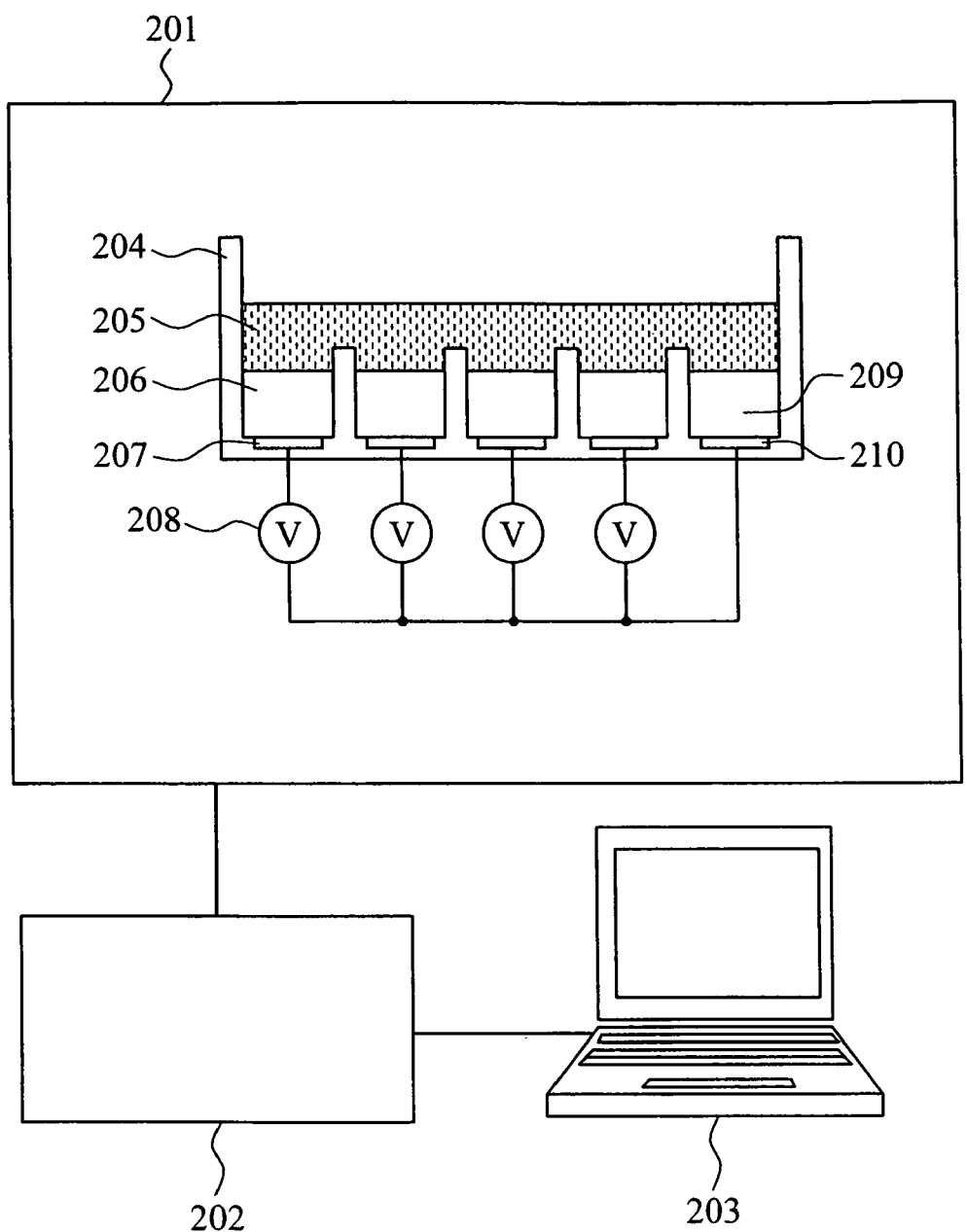
FIG. 2 is a block diagram indicating one example of an analyzer for analyzing a small amount of liquid according to present invention.

FIG. 2 is a block diagram indicating one example of a small analyzer according to the present invention. An analyzer of the present example includes a measuring section 201, a signal processing circuit 202, and a data processing device 203. The measuring section 201 includes a measuring container 204, a medium 205, a sample solution 206, a measuring electrode 207, a voltmeter 208, a reference electrode internal liquid 209 and a reference electrode 210. The measuring container 204 is divided into a plurality of vessels. The measuring electrodes 207 are each arranged in each vessel; and the reference electrode 210 is arranged in one vessel. The voltmeters 208 are each connected to each of the electrodes 107, and the other end of the voltmeter 208 is communicated with the reference electrode 210. The sample solution 206 is present in each vessel in which each of the measuring electrodes 207 is arranged, and the reference electrode internal liquid 209 is present in a vessel in which the reference electrode 210 arranged. The medium 205 is present across each vessel in which each measuring electrode is present and the vessel in which the reference electrode is present. The medium 205 makes contact with each of the sample solutions 206 and the reference electrode internal solution 209.

One example of measuring procedures will be depicted. First, the sample solution 206 is poured into each vessel in which each measuring electrode is present. At this time, the sample solution 206 is poured so as not to overflow from a vessel. The reference electrode internal liquid 209 is poured into the vessel in which the reference electrode is present. Next, the medium 205 is poured into the measuring container 204 across the plurality of the vessels. When the specific gravity of the medium 205 is larger than those of the sample solution 206 and the reference electrode internal liquid 209, the medium 205 is carefully poured so as not to enter into the lower part of the sample solution 206 and the reference electrode internal liquid 209. Finally, a potential indicated by each of the voltmeters 208 communicated with each of the measuring electrodes 207 is read out.

The sample solution 206 and the reference electrode internal liquid 209 may be poured so as to almost overflow from each vessel in order to make the sample solution 206 and the reference electrode internal liquid 209 contact the medium 205 readily. In addition, after the medium 205 is poured, each of the sample solutions 206 and the reference electrode internal liquid 209 are poured into each vessel in some cases as well. Different solutions such as a sample and a reagent may be each poured into one vessel so that those different solutions react with each other in the vessel.

A liquid immiscible with water is used as the medium 205. Use of a liquid immiscible with water prevents the sample solutions 106 in a plurality of vessels and the reference electrode internal liquid 209 from mixing with each other and makes it possible to read interfacial potentials between the electrodes 207 arranged within the plurality of vessels and the sample solutions 206. For example, although the interfacial potentials between the electrodes 207 arranged in a plurality of vessels and the sample solutions 206 can be read also by use of a liquid miscible with water as the medium 205, there are fears that the liquid would mix with each of the sample solutions 206, that the sample solutions 206 would mix with each other, and that each of the sample solutions 206 would mix with the reference electrode internal liquid 209.

An apparatus may be miniaturized by setting one vessel as a reference electrode as compared with the case where a reference electrode is separately provided. Further, wiring for potential measurement can be made short in some cases, which is advantageous in terms of prevention of noise and leak current. When stability is lowered due to a reference electrode made small, a same electrode as the reference electrode 210 is used for a part of the measuring electrodes 207 to make vessels into which the reference electrode internal liquid 209 are poured instead of the sample solution 206, and these vessels, i.e. electrodes, made to be sub-reference electrodes. When the reference electrode 210 and a sub-reference electrode properly function, the potential difference between these two electrodes becomes 0. Therefore, if the potential difference between these two electrodes is not 0, the stability of the reference electrode is improved in some cases when the other measured potential is corrected using the potential of the reference electrode. For example, the potential V' after the correction is evaluated by the equation $V'=V-V_{ref}/2$, where V represents a potential that is measured at one of the measuring potential 207 and $V_{ref}$ represents a potential that is measured at the sub-reference electrode. Furthermore, the correction of use of the potentials of a plurality of sub-reference electrodes further improves the stability in some cases. As another application of the sub-reference electrode, a potential gradient present inside the medium 205 can be compensated in some cases. If the electric conductivity of the medium 205 is insufficient, a potential gradient may be generated inside the medium 205. Sub-reference electrodes are dispersed and arranged and each potential difference is measured, so that the potential gradient inside the medium 205 can be estimated. The correction of a measurement at each of the measuring electrodes 207 using the potential gradient value makes it possible to decrease the influence of a potential gradient inside the medium 205.

Placing the medium 205 so as to cover the sample solution 206 renders it possible to prevent the evaporation of the sample solution 206. A small amount of sample solution renders the effect of evaporation of a sample solution remarkable. At the time, the evaporation of a sample solution can be restrained with the sample solution covered with some material immiscible with the sample solution, and the placement of the medium 205 like the present example enables the restraint of the evaporation and the measurement of the potential to be simultaneously performed.

The medium 205 desirably contains an organic salt. Alternatively, a liquid organic salt is desirably used. When the medium 205 has insulating properties, a potential gradient may be generated within the medium. In this case, the potentials within media near each of the vessels are not equal to each other, so it is difficult to more precisely measure the interfacial potential between the electrode 207 arranged in each vessel and the sample solution 206. The value $V_n$ of each voltmeter 208 communicated with the electrode 207 arranged within each vessel n is given by:

$$V_n = V_{Ref} + \Phi_{Ref} + V_{Grad,n} + \Phi_{pho,n} + \Phi_n$$

wherein $V_{Ref}$: Interfacial potential of the reference electrode 210, $\Phi_{Ref}$: Interfacial potential between the reference electrode internal liquid 209 and the medium 205, $V_{Grad,n}$: Potential gradient between the vicinities of the reference electrode internal liquid 209 and each vessel n, within the medium 205, $\Phi_{pho,n}$: Interfacial potential between the medium 205 and each of the sample solutions 206 within each of the vessels n, and $\Phi_n$: Interfacial potential between the electrode 207 arranged within each of the vessels n and the sample solution 206.

On the basis of the above equation, $\Phi_n$ can be determined from $V_n$. Here, $V_{Ref}$ and $\Phi_{Ref}$ do not depend on the vessel n. Assuming that $\Phi_{pho,n}$ is not largely changed between each sample solution, $\Phi_n$ can be determined from $V_n$ if $V_{Grad,n}$ is not present. However, if $V_{Grad,n}$ is present, a precise $\Phi_n$ cannot be determined from $V_n$. If an organic salt dissolves in the medium 205, the organic salt becomes a supporting electrolyte, whereby $V_{Grad,n}$ can be decreased, thereby being capable of more precisely determining $\Phi_n$ from $V_n$. Furthermore, the medium 205 or the sample solution 206 desirably contains a salt that can dissolve in both the liquids. The presence of such a salt enables $\Phi_{pho,n}$ to be decrease, thereby being able to more precisely obtain $\Phi_n$ from $V_n$.

The combinations of the reference electrode 210 and the reference electrode internal liquid 209 that can be used include a silver-silver chloride electrode and an aqueous potassium chloride solution, a silver-silver chloride electrode and an aqueous sodium chloride solution, an electrode of a noble metal such as gold, silver, copper or platinum and ferrocene/ferrocenium ion, an electrode of a noble metal such as gold, silver, copper or platinum and ferricyanide/ferrocyanide, and the like. The measuring electrodes 207 that can be used include noble metals such as gold, silver, copper and platinum, the metals above modified with an alkanethiol single molecular film, and further electrodes modified with an ion-sensitive membrane, and the like. The mediums 205 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

Figure 3A:
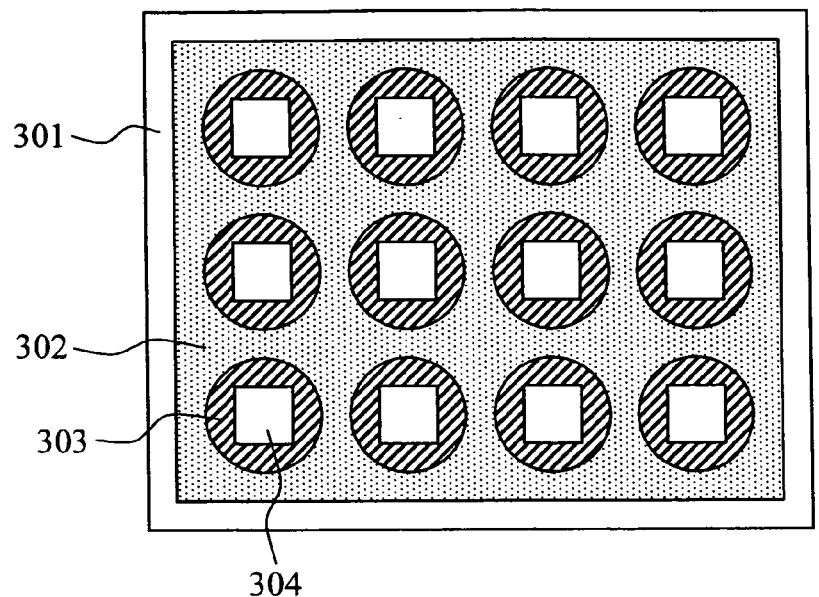
FIG. 3 is a diagram indicating one example of a measuring section of an analyzer for analyzing a small amount of liquid according to present invention.
Figure 3B:
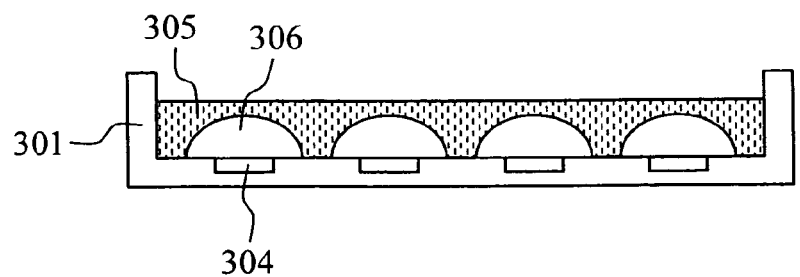

FIG. 3 is a diagram indicating another example of a measuring section of a small analyzer according the present invention. FIG. 3(A) is a diagram of a measuring section not in use, viewed from above; FIG. 3(B) is a sectional view of the measuring section in use. The present measuring section includes a measuring container 301, a hydrophobic surface 302, a hydrophilic surface 303 and an electrode 304. Upon measurement, a sample solution 306 is arranged on the hydrophilic surface 303 and a medium 305 is arranged on the hydrophobic surface 302. The medium 305 is in a continuous state and makes contact with each of the sample solutions 306.

The measurement procedure is in the following. First, each of the sample solutions 306 is arranged on each of the hydrophilic surfaces 303. Next, the medium 305 is poured into the container. At this time, attention must be paid such that each of the sample solutions 306 does not move from each of the hydrophilic surfaces 303. Then, a potential indicated by a voltmeter connected to each of the electrodes 304 as in another example is read out. At this time, a reference electrode may be arranged so as to make contact with the medium 305, or a reference electrode internal liquid may be placed thereon using one of the measuring electrodes as a reference electrode.

The inside of the measuring container is divided into a hydrophilic surface and a hydrophobic surface, so that a sample solution can be arranged without a concave and a convex disposed within the measuring container. This makes it possible to improve the efficiency of cleaning. In addition, even if the specific gravity of a medium is larger than that of a sample solution, measurement can be carried out without the medium being not entered into the lower part of the sample solution if the absorbability of the sample solution onto the hydrophilic surface is larger than the buoyancy of the medium.

The reference electrodes that can be used include, in addition to a silver-silver chloride electrode, a standard hydrogen electrode, a saturated calomel electrode, a mercury-mercurous sulfate electrode and a mercurous oxide electrode, a reference electrode that uses as a standard potential an electrode reaction of a reversible redox system like ferrocene/ferrocenium ion, or ferricyanide/ferrocyanide. The electrodes 304 that can be used include noble metals such as gold, silver, copper and platinum, the metals above modified with an alkanethiol single molecular film, and further electrodes modified with an ion-sensitive membrane, and the like. The mediums 305 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

As the hydrophilic surface, used are a surface treated with plasma, a surface coated with a single molecular film of a silane coupling agent or the like, a surface coated with an LB film, or the like. As the hydrophobic surface, used are a surface treated with fluorine oil or chlorofluorocarbon, a surface coated with a single molecular film of a silane coupling agent or the like, a surface coated with an LB film, or the like.

Figure 4A:
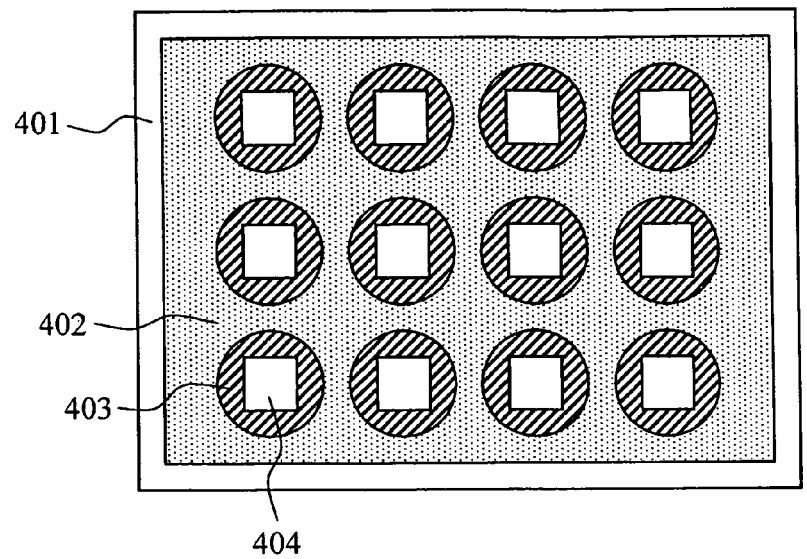
FIG. 4 is a diagram indicating one example of a measuring section of an analyzer for analyzing a small amount of liquid according to present invention.
Figure 4B:
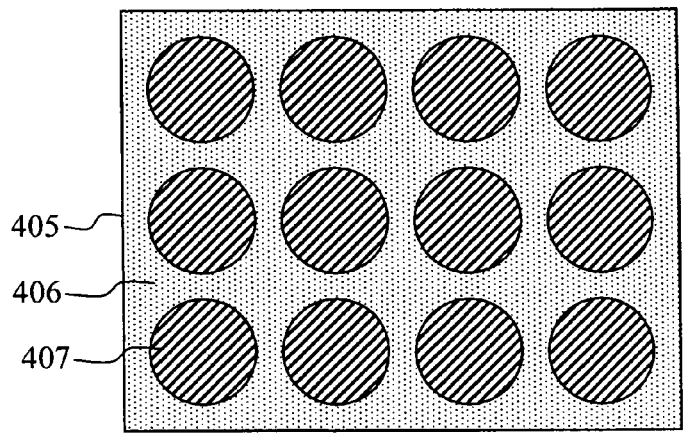
Figure 4C:
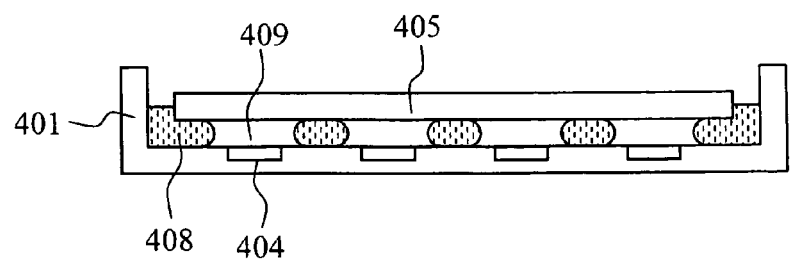

FIG. 4 is a diagram indicating another example of a measuring section of a small analyzer according the present invention. The present measuring section includes two portions. FIGS. 4(A) and 4(B) are diagrams of the two portions viewed from above and below; FIG. 4(C) is a sectional view of a measuring section in use. The lower portion of the present measuring section includes a measuring container 401, a hydrophobic surface 402, a hydrophilic surface 403 and an electrode 404. The upper portion of the present measuring section includes a container lid 405, a hydrophobic surface 406 and a hydrophilic surface 407. Upon measurement, the lower portion is placed so as to be opposite to the upper portion; the sample solution 409 is placed so as to be sandwiched by the hydrophilic surfaces 403 and 407; the medium 408 is placed so as to be sandwiched by the hydrophobic surfaces 402 and 406.

The procedure of measurement is in the following. First, the empty measuring container 401 is prepared and each of the sample solutions 409 is placed on each of the hydrophilic surfaces 403. Next, the container lid 405 is placed on the measuring container 401 and each of the sample solutions 409 is sandwiched by each of the hydrophilic surfaces 403 and 407. A spacer may be placed between the measuring container 401 and the container lid 405 in order to specify the interval between the measuring container 401 and the container lid 405. In addition, a claw is disposed on the side of the container lid 405 and the claw may be hung on the measuring container 401 to maintain the interval between the measuring container 401 and the container lid 405. Then, the medium 408 is poured into the container. At this time, attention is paid such that each of the sample solutions 409 is not moved from each of the hydrophilic surfaces 403 and 407. Additionally, attention is paid such that air does not remain within the container. Next, a potential indicated by a voltmeter connected to each of the electrodes 404 as in another example is read out. At this time, a reference electrode may be arranged so as to make contact with the medium 408, or a reference electrode internal liquid may be poured onto one or more of the hydrophilic surfaces for the purpose of using for a reference electrode. Although each of the electrodes 404 is present in the lower portion, it may be present in the upper portion.

The inside of the measuring container is divided into a hydrophobic surface and a hydrophilic surface, so that a sample solution can be arranged without a concave and a convex disposed within the measuring container. This makes it possible to improve the efficiency of cleaning. In addition, even if the specific gravity of a medium is larger than that of a sample solution, measurement can be carried out without the medium being not entered into the lower part of the sample solution if the absorbability of the sample solution onto the hydrophilic surface is larger than the buoyancy of the medium.

The sample solution 409 is sandwiched between the hydrophilic surfaces 403 of the measuring container 401 and the hydrophilic surfaces 407 of the container lid 405, whereby measurement can be carried out without a medium being not entered into the lower part of the sample solution even if the specific gravity of the medium is larger than that of the sample solution, since the absorbability of the sample solution onto the hydrophilic surface is larger than that of the case without the sandwiching. Additionally, since the sample solution is pushed down by the hydrophilic surface of the upper portion, even if a small amount of medium is entered into the lower part of the sample solution, measurement can be performed without any problems as long as the sample solution 409 is kept in contact with the electrode 404.

The reference electrodes that can be used include, in addition to a silver-silver chloride electrode, a standard hydrogen electrode, a saturated calomel electrode, a mercury-mercurous sulfate electrode and a mercurous oxide electrode, a reference electrode that uses as a standard potential an electrode reaction of a reversible redox system like ferrocene/ ferrocenium ion, or ferricyanide/ferrocyanide. The electrodes 404 that can be used include noble metals such as gold, silver, copper and platinum, the metals above modified with an alkanethiol single molecular film, and further electrodes modified with an ion-sensitive membrane, and the like. The mediums 408 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl) imide, and the like.

As the hydrophilic surface, used are a surface treated with plasma, a surface coated with a single molecular film of a silane coupling agent or the like, a surface coated with an LB film, or the like. As the hydrophobic surface, used are a surface treated with fluorine oil or chlorofluorocarbon, a surface coated with a single molecular film of a silane coupling agent or the like, a surface coated with an LB film, or the like.

Figure 5:
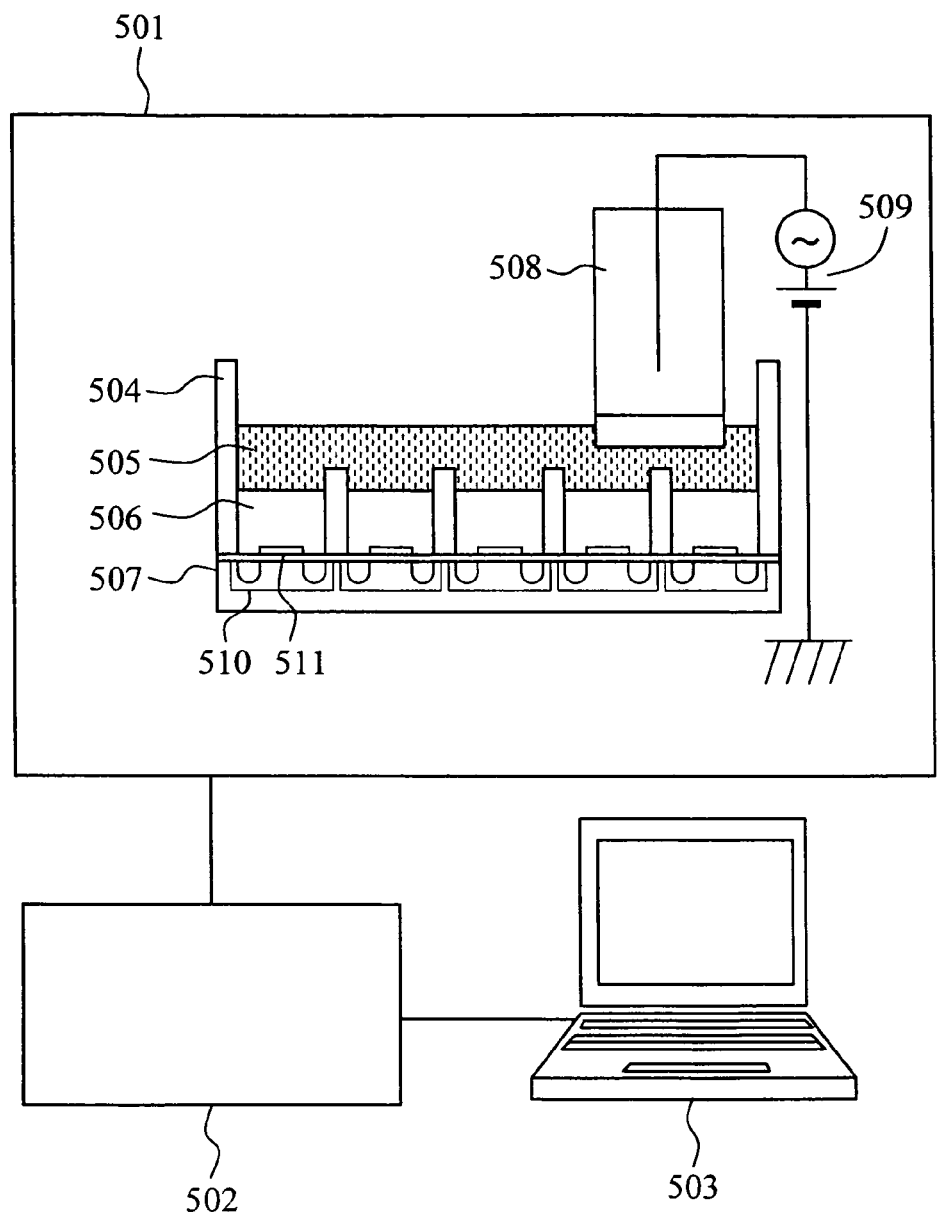
FIG. 5 is a block diagram indicating one example of an analyzer for analyzing a small amount of liquid according to present invention.

FIG. 5 is a block diagram indicating one example of a small analyzer according to the present invention. An analyzer of the present example includes a measuring section 501, a signal processing circuit 502, and a data processing device 503. The measuring section 501 includes a measuring container 504, a medium 505, a sample solution 506, a substrate 507, a reference electrode 508, and a power source 509. The substrate 507 includes a plurality of pairs of field effect transistors 510 and electrodes 511, and each pair is arranged corresponding to a plurality of vessels in the measuring container 504. The gate part of the field effect transistor 510 is communicated with the electrode 511 and the potential of the electrode 511 can be measured by the field effect transistor 510. The sample solution 506 is present in each vessel and the medium 505 is present across the plurality of the vessels. The medium 505 makes contact with a plurality of the sample solutions 506 and the reference electrode 508.

One example of measuring procedures will be depicted. First, the sample solution 506 is poured into each vessel. At this time, the sample solution 506 is poured so as not to overflow from a vessel. Next, the medium 505 is poured into the measuring container 504 across the plurality of the vessels. When the specific gravity of the medium 505 is larger than that of the sample solution 506, the medium 505 is carefully placed so as not to enter into the lower part of the sample solution 506. Then, the reference electrode 508 is arranged such that a liquid junction makes contact with the medium 505. Finally, a potential of each of the electrodes 511 arranged within each vessel is read out by the field effect transistor 510.

The sample solution 506 may also be poured so as to almost overflow from each vessel in order to make the sample solution 506 contact the medium 505 readily. In addition, after the medium 505 is poured thereinto, each of the sample solutions 506 is poured into each vessel in some cases as well. Different solutions such as a sample and a reagent may be each poured into one vessel so that those different solutions react with each other in the vessel.

One example of the method of measuring a potential of the electrode 511 by use of the field effect transistor 510 will be depicted. A voltage is applied to the reference electrode 508 from the power source 509. At this time, the power source 509 may be a direct current source or an alternating current source. Next, voltage-current characteristics are measured between the source and the drain of a field effect transistor. A semiconductor parameter analyzer or its imitation circuit, or the like can be used for the measurement. The voltage-current characteristics measured are converted into a potential of the electrode 511 by use of voltage-current characteristics measured in advance.

A liquid immiscible with water is used as the medium 505. Use of a liquid immiscible with water prevents the sample solutions 506 in a plurality of vessels from mixing with each other and makes it possible to read interfacial potentials between the electrodes 511 arranged within the plurality of vessels and the sample solutions 506. For example, although the interfacial potentials between the electrodes 511 arranged in a plurality of vessels and the sample solutions 506 can be read also by use of a liquid miscible with water as the medium 505, there are fears that the liquid would mix with each of the sample solutions 506 and further that each of the sample solutions 506 would mix with each other.

The measurement of the potential difference between the reference electrode 508 and the electrode 511 arranged in each vessel via the medium 505 enables a reference electrode having a cross section larger than the cross section of each vessel to be employed. The measurement of the potential difference between the reference electrode 508 and the electrode 511 arranged within each vessel without using the medium 105 may be done, for example, by arrangement of a reference electrode within each vessel. However, in this case, the cross section of each vessel must have a size that can embrace the cross section of the reference potential. Accordingly, if an interfacial potential between the electrode 511 arranged within each vessel and the sample solution 506 is read out using a smaller amount of the sample solution 506, the cross section of a reference electrode needs to be made small. A small reference electrode has disadvantages as compared with a large reference electrode in terms of the clogging of a liquid junction, stability of the potential and life. In an actual case, a quasi-electrode such as a silver-silver chloride electrode not having an internal liquid is frequently used as a small reference electrode; however, this electrode is further disadvantageous in stability and life.

Reading out the interfacial potential between the electrode 511 arranged within each vessel and the sample solution 506 via the medium 505 enables reference electrodes the number of which is smaller than that of vessels to be employed. Reading out the interfacial potential between the electrode 511 arranged within each vessel and the sample solution 506 without using the medium 505 may be done, for example, by arrangement of a reference electrode within each vessel. However, in this case, reference electrodes the number of which is equal to that of vessels are needed. Thus, the apparatus becomes costly, and, in some cases, the variation of potentials between each of reference electrodes may create a problem. Alternatively, one reference electrode is alternately placed in each vessel and the interfacial potential between the electrode 511 arranged within each vessel and the sample solution 506 may be read out one by one. In this case, the above mentioned cost and the variation of the potential between each of the reference electrodes do not create a problem, while the reference electrodes need to be washed for every potential measurement, which is time-consuming, in order to prevent mixing of each of the sample solutions 506, and the case sometimes needs time for measurement due to every potential difference being read out one by one, as compared with the case of reading a plurality of potential differences at one time.

Placing the medium 505 so as to cover the sample solution 506 renders it possible to prevent the evaporation of the sample solution 506. A small amount of sample solution renders the effect of evaporation of a sample solution remarkable. At the time, the evaporation of a sample solution can be restrained with the sample solution covered with some material immiscible with the sample solution, and the placement of the medium 505 like the present example enables the restraint of the evaporation and the measurement of the potential to be simultaneously performed.

The medium 505 desirably contains an organic salt. Alternatively, a liquid organic salt is desirably used. When the medium 505 has insulating properties, a potential gradient may be generated within the medium. In this case, the potentials within media near each of the vessels are not equal to each other, so it is difficult to more precisely measure the interfacial potential between the electrode 511 arranged in each vessel and the sample solution 506. The potential difference $V_n$ between the electrode 511 arranged within each vessel n measured by the field effect transistor 510 and the reference electrode 508 is given by:

$$V_n = V_{Ref} + \Phi_{Ref} + V_{Grad,n} + \Phi_{pho,n} + \Phi_n$$

wherein $V_{Ref}$: Interfacial potential of the reference electrode 508, $\Phi_{Ref}$: Interfacial potential between an internal liquid of the reference electrode 508 and the medium 505, $V_{Grad,n}$: Potential gradient between the vicinities of the reference electrode 508 and each vessel n, within the medium 505, $\Phi_{pho,n}$: Interfacial potential between the medium 505 and each of the sample solutions 506 within each of the vessels n, and $\Phi_n$: Interfacial potential between the electrode 511 arranged within each of the vessels n and the sample solution 506.

On the basis of the above equation, $\Phi_n$ can be determined from $V_n$. Here, $V_{Ref}$ and $\Phi_{Ref}$ do not depend on the vessel n. Assuming that $\Phi_{pho,n}$ is not largely changed between each sample solution, $\Phi_n$ can be determined from $V_n$ if $V_{Grad,n}$ is not present. However, if $V_{Grad,n}$ is present, a precise $\Phi_n$ cannot be determined from $V_n$. If an organic salt dissolves in the medium 505, the organic salt becomes a supporting electrolyte, whereby $V_{Grad,n}$ can be decreased, thereby being capable of more precisely determining $\Phi_n$ from $V_n$. Furthermore, the medium 505 or the sample solution 506 desirably contains a salt that can dissolve in both the liquids. The presence of such a salt enables $\Phi_{pho,n}$ to be decrease, thereby being able to more precisely obtain $\Phi_n$ from $V_n$.

The reference electrodes 508 that can be used include, in addition to a silver-silver chloride electrode, a standard hydrogen electrode, a saturated calomel electrode, a mercurous sulfate electrode and a mercurous oxide electrode, a reference electrode that uses as a standard potential an electrode reaction of a reversible redox system like ferrocene/ferrocenium ion, or ferricyanide/ferrocyanide. The electrodes 511 that can be used include noble metals such as gold, silver, copper and platinum, the metals above modified with an alkanethiol single molecular film, and further electrodes modified with an ion-sensitive membrane, and the like. The mediums 505 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

Figure 6:
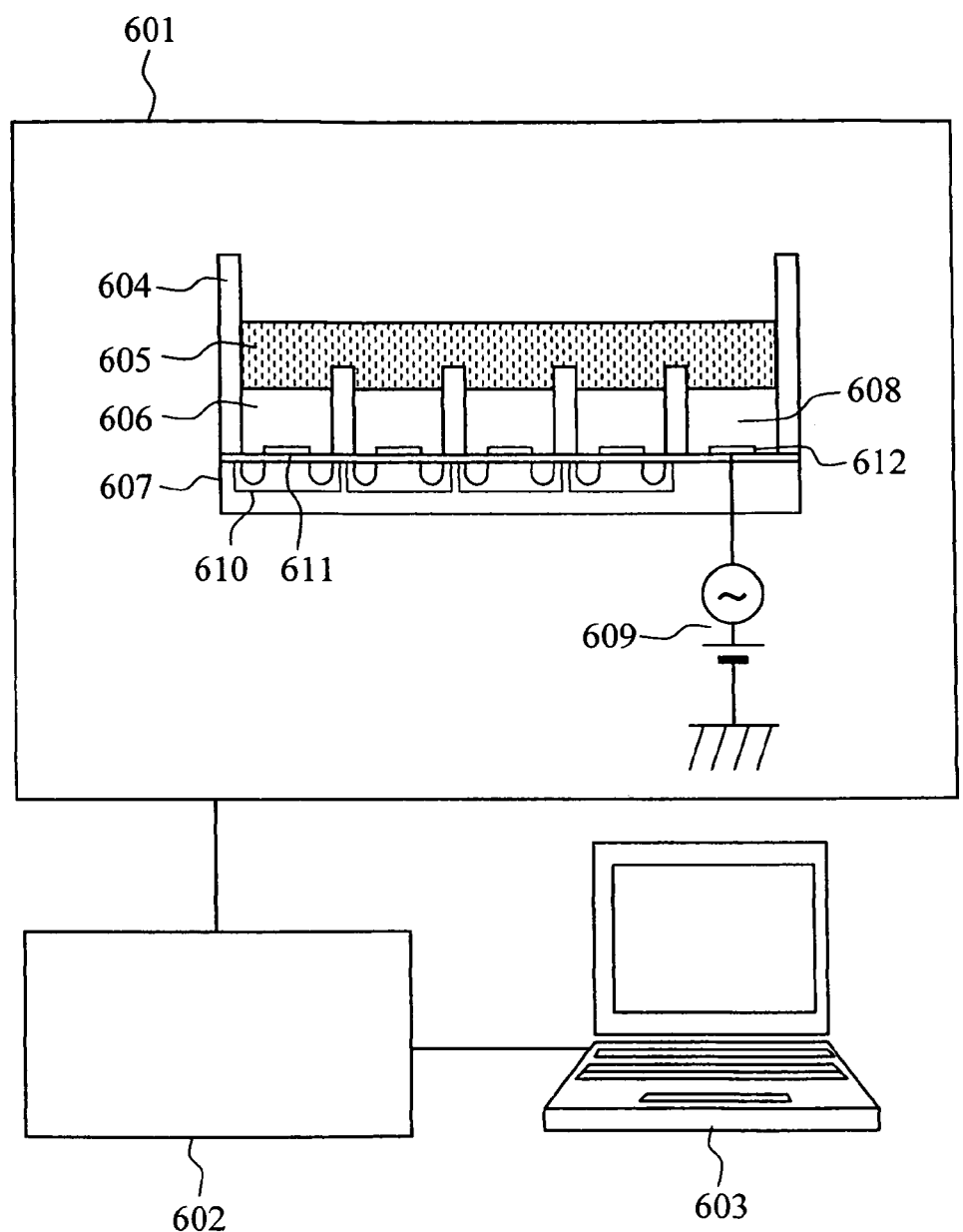
FIG. 6 is a block diagram indicating one example of an analyzer for analyzing a small amount of liquid according to present invention.

FIG. 6 is a block diagram indicating one example of a small analyzer according to the present invention. An analyzer of the present example includes a measuring section 601, a signal processing circuit 602, and a data processing device 603. The measuring section 601 includes a measuring container 604, a medium 605, a sample solution 606, a substrate 607, and a power source 609. The substrate 607 includes a plurality of pairs of field effect transistors 610 and measuring electrodes 611, and each pair is arranged corresponding to a plurality of vessels in the measuring container 604. The gate part of the field effect transistor 610 is communicated with the electrode 611 and the potential of the measuring electrode 611 can be measured by the field effect transistor 610. In addition, a reference electrode 612 connected to the power source 609 is present in the substrate, and a reference electrode internal liquid 608 is present in a vessel in which the reference electrode 612 is present. The sample solution 606 is present in each vessel and the medium 605 is present across the plurality of the vessels. The medium 605 makes contact with a plurality of the sample solutions 606 and the reference electrode internal liquid 608.

One example of measuring procedures will be depicted. First, the sample solution 506 is poured into each vessel. At this time, the sample solution 606 is poured so as not to overflow from a vessel. Next, the reference electrode internal liquid 608 is poured into a vessel in which the electrode 612 is present. Then, the medium 605 is poured into the measuring container 604 across a plurality of the vessels. When the specific gravity of the medium 605 is larger than those of the sample solution 606 and the reference electrode internal liquid 608, the medium 605 is carefully placed so as not to enter into the lower parts of the sample solution 606 and the reference electrode internal liquid 608. Finally, the potential of each of the electrodes 611 arranged within each vessel is read out by the field effect transistor 610.

The sample solution 606 and the reference electrode internal liquid 608 may also be poured so as to almost overflow from each vessel in order to make the sample solution 606 and the reference electrode internal liquid 608 contact the medium 605 readily. In addition, after the medium 605 is poured thereinto, each of the sample solutions 606 may also be poured into each vessel. Different solutions such as a sample and a reagent may be each poured into one vessel so that those different solutions react with each other in the vessel.

One example of the method of measuring a potential of the electrode 611 by use of the field effect transistor 610 will be depicted. A voltage is applied to the reference electrode 612 from the power source 609. At this time, the power source 609 may be a direct current source or an alternating current source. Next, voltage-current characteristics are measured between the source and the drain of the field effect transistor 610. A semiconductor parameter analyzer or its imitation circuit, or the like can be used for the measurement. The voltage-current characteristics measured are converted into a potential of the electrode 611 by use of voltage-current characteristics measured in advance.

A liquid immiscible with water is used as the medium 605. Use of a liquid immiscible with water prevents the sample solutions 606 in a plurality of vessels and the reference electrode internal liquid 608 from mixing with each other and makes it possible to read interfacial potentials between the electrodes 611 arranged within the plurality of vessels and the sample solutions 606. For example, although the interfacial potentials between the electrodes 607 arranged in a plurality of vessels and the sample solutions 606 can be read also by use of a liquid miscible with water as the medium 605, there are fears that the liquid would mix with each of the sample solutions 606, that the sample solution 606 would mix with each other, and further that each of the sample solutions 606 would mix with the reference electrode internal liquid 608.

An apparatus may be miniaturized by setting one vessel as a reference electrode as compared with the case where a reference electrode is separately disposed. Further, wiring for potential measurement can be made short in some cases, which is advantageous in terms of prevention of noise and leak current. When stability is lowered due to a reference electrode made small, a same electrode as the reference electrode 612 is used for a part of the measuring electrodes 611 to make vessels into which the reference electrode internal liquid 608 are poured instead of the sample solution 606, and these vessels, i.e. electrodes, are used as sub-reference electrodes. When the reference electrode 612 and a sub-reference electrode properly function, the potential difference between these two electrodes becomes 0. Therefore, if the potential difference between these two electrodes is not 0, the stability of the reference electrode is improved in some cases when the other measured potential is corrected using the potential of the reference electrode. For example, the potential V' after the correction is evaluated by the equation V'=V-V$_{ref}$/2, where V represents a potential that is measured at one of the measuring potential 611 and V$_{ref}$ represents a potential that is measured at the sub-reference electrode. Furthermore, the correction of use of the potentials of a plurality of sub-reference electrodes further improves the stability in some cases. As another application of the sub-reference electrode, a potential gradient present inside the medium 605 can be compensated in some cases. If the electric conductivity of the medium 605 is insufficient, a potential gradient may be generated inside the medium 605. Sub-reference electrodes are dispersed and arranged and each potential difference is measured, so that the potential gradient inside the medium 605 can be estimated. The correction of a measurement at each of the measuring electrodes 611 using the potential gradient value makes it possible to decrease the influence of a potential gradient inside the medium 605.

Placing the medium 605 so as to cover the sample solution 606 renders it possible to prevent the evaporation of the sample solution 606. A small amount of sample solution renders the effect of evaporation of a sample solution remarkable. At the time, the evaporation of a sample solution can be restrained with the sample solution covered with some material immiscible with the sample solution, and the placement of the medium 605 like the present example enables the restraint of the evaporation and the measurement of the potential to be simultaneously performed.

The medium 605 desirably contains an organic salt. Alternatively, a liquid organic salt is desirably used. When the medium 605 has insulating properties, a potential gradient may be generated within the medium. In this case, the potentials within media near each of the vessels are not equal to each other, so it is difficult to more precisely measure the interfacial potential between the electrode 611 arranged in each vessel and the sample solution 606. The potential difference V$_n$ between the electrode 611 arranged within each vessel n measured by the field effect transistor 610 and the reference electrode 612 is given by:

$$V_n = V_{Ref} + \Phi_{Ref} + V_{Grad,n} + \Phi_{pho,n} + \Phi_n$$

wherein

V$_{Ref}$: Interfacial potential of the reference electrode 612, $\Phi_{Ref}$: Interfacial potential between the reference electrode internal liquid 608 and the medium 605, V$_{Grad,n}$: Potential gradient between the vicinities of the reference electrode 612 and each vessel n, within the medium 605, $\Phi_{pho,n}$: Interfacial potential between the medium 605 and each of the sample solutions 606 within each of the vessels n, and $\Phi_n$: Interfacial potential between the electrode 611 arranged within each of the vessels n and the sample solution 606.

On the basis of the above equation, $\Phi_n$ can be determined from V$_n$. Here, V$_{Ref}$ and $\Phi_{Ref}$ do not depend on the vessel n. Assuming that $\Phi_{pho,n}$ is not largely changed between each sample solution, $\Phi_n$ can be determined from V$_n$ if V$_{Grad,n}$ is not present. However, if V$_{Grad,n}$ is present, a precise $\Phi_n$ cannot be determined from V$_n$. If an organic salt dissolves in the medium 605, the organic salt becomes a supporting electrolyte, whereby V$_{Grad,n}$ can be decreased, thereby being capable of more precisely determining $\Phi_n$ from V$_n$. Furthermore, the medium 605 or the sample solution 606 desirably contains a salt that can dissolve in both the liquids. The presence of such a salt enables $\Phi_{pho,n}$ to be decrease, thereby being able to more precisely obtain $\Phi_n$ from V$_n$. The salts that can dissolve in both the liquids and that can be used include, for example, tetramethylammonium, and the like.

The combinations of the reference electrode 612 and the reference electrode internal liquid 608 that can be used include a silver-silver chloride electrode and an aqueous potassium chloride solution, a silver-silver chloride electrode and an aqueous sodium chloride solution, an electrode of a noble metal such as gold, silver, copper or platinum and ferrocene/ferrocenium ion, an electrode of a noble metal such as gold, silver, copper or platinum and ferricyanide/ferrocyanide, and the like. The electrodes 611 that can be used include noble metals such as gold, silver, copper and platinum, the metals above modified with an alkanethiol single molecular film, and further electrodes modified with an ion-sensitive membrane, and the like. The mediums 605 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

Figure 7A:
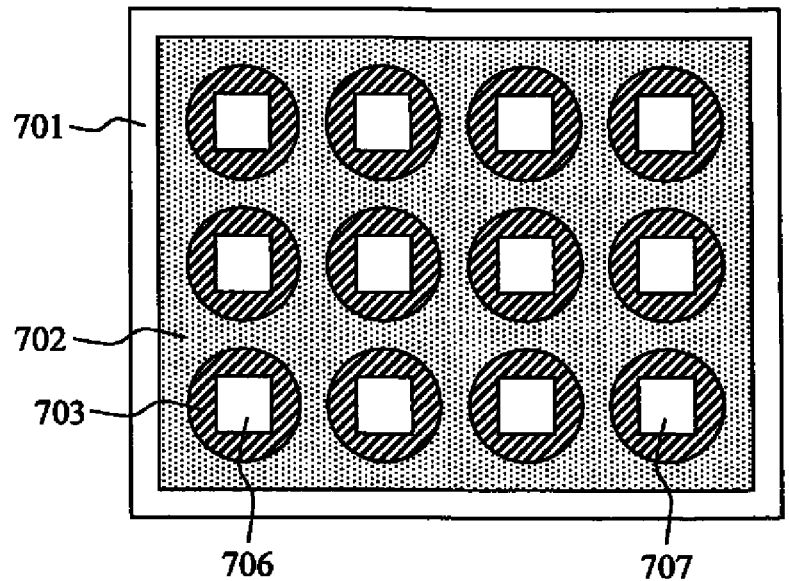
FIG. 7 is a diagram indicating one example of a measuring section of an analyzer for analyzing a small amount of liquid according to present invention.
Figure 7B:
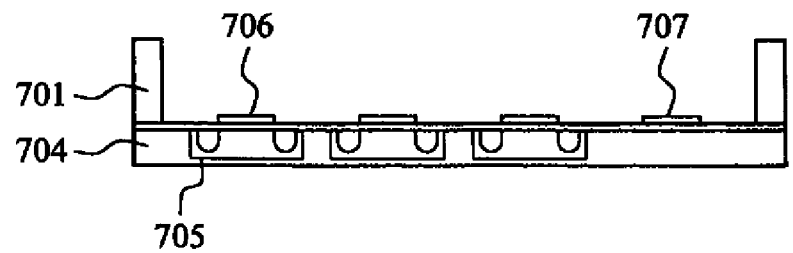
Figure 7C:
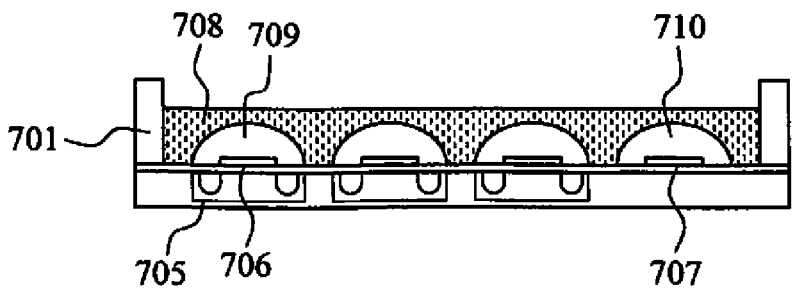
Figure 8A:
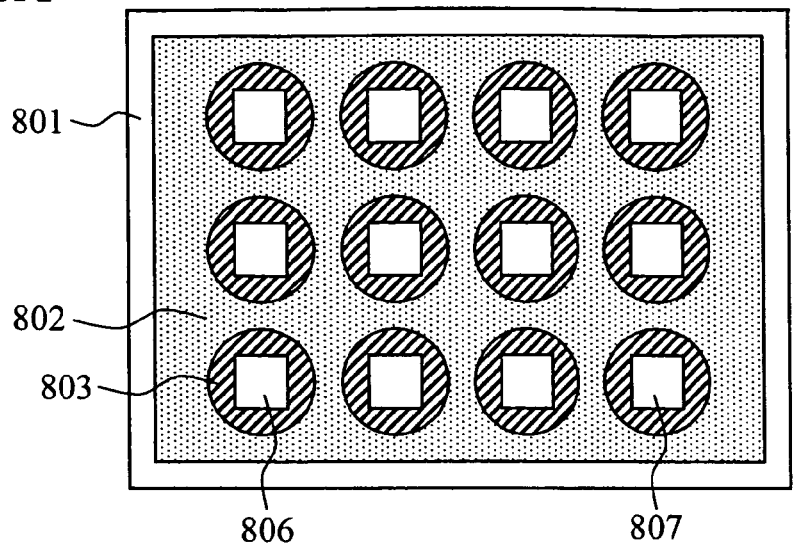
FIG. 8 is a diagram indicating one example of a measuring section of an analyzer for analyzing a small amount of liquid according to present invention.
Figure 8B:
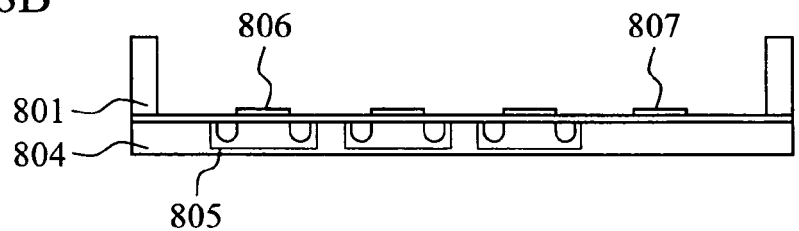
Figure 8C:
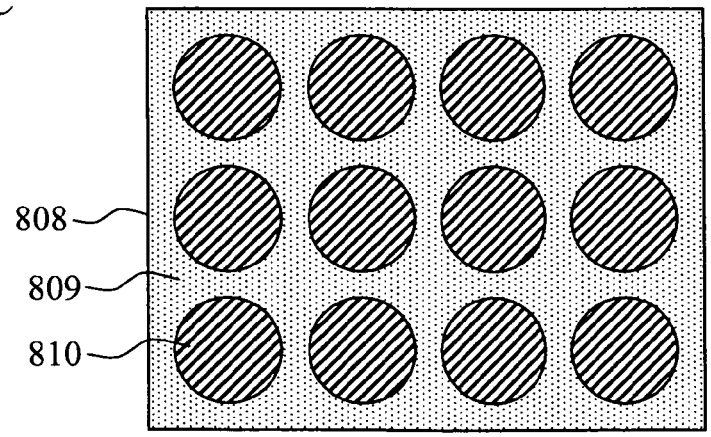
Figure 8D:
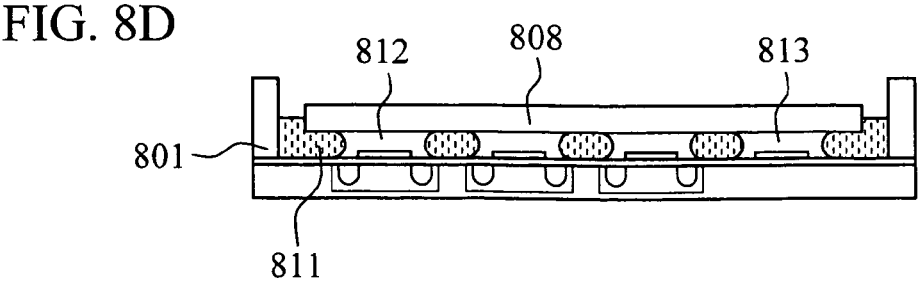

FIG. 7 is a diagram indicating another example of a measuring section of a small analyzer according the present invention. FIG. 7(A) is a diagram of a measuring section not in use, viewed from above; FIG. 7(B) is a sectional view of the measuring section not in use; FIG. 7(C) is a sectional view of the measuring section in use. The present measuring section includes a measuring container 701, a hydrophobic surface 702, a hydrophilic surface 703 and a substrate 704. The substrate 704 includes a plurality of pairs of field effect transistors 705 and measuring electrodes 706. The gate part of the field effect transistor 705 is connected to the measuring electrode 706 to thereby measure the potential of the measuring electrode 706 by means of the field effect transistor 705. In addition, the substrate includes a reference electrode 707. Upon measurement, a sample solution 709 is arranged on the hydrophilic surface 703 and a medium 708 is arranged on the hydrophobic surface 702. A reference electrode internal liquid 710 is placed on the reference electrode 707.

The measurement procedure is in the following. First, each of the sample solutions 709 is arranged on each of the hydrophilic surfaces 703. The reference electrode internal liquid 710 is placed on the electrode 707. Next, the medium 708 is poured into the container. At this time, attention must be paid such that each of the sample solutions 709 and the reference electrode internal liquid 710 do not move from each of the hydrophilic surfaces 703. Then, a potential indicated by a voltmeter connected to each of the electrodes 706 as in another example is read out with use of the field effect transistor.

One example of the method of measuring a potential of the measuring electrode 706 by use of the field effect transistor 705 will be depicted. A voltage is applied to the reference electrode 707 in contact with the reference electrode internal liquid 710 from the power source separately provided. At this time, the power source may be a direct current source or an alternating current source. Next, voltage-current characteristics are measured between the source and the drain of the field effect transistor 705. A semiconductor parameter analyzer or its imitation circuit, or the like can be used for the measurement. The voltage-current characteristics measured are converted into a potential of the electrode 706 by use of voltage-current characteristics measured in advance.

The inside of the measuring container is divided into a hydrophilic surface and a hydrophobic surface, so that a sample solution can be arranged without a concave and a convex disposed within the measuring container. This makes it possible to improve the efficiency of cleaning. In addition, even if the specific gravity of a medium is larger than that of a sample solution, measurement can be carried out without the medium being not entered into the lower part of the sample solution if the absorbability of the sample solution onto the hydrophilic surface is larger than the buoyancy of the medium.

The combinations of the reference electrode 707 and the reference electrode internal liquid 710 that can be used include a silver-silver chloride electrode and an aqueous potassium chloride solution, a silver-silver chloride electrode and an aqueous sodium chloride solution, an electrode of a noble metal such as gold, silver, copper or platinum and ferrocene/ferrocenium ion, an electrode of a noble metal such as gold, silver, copper or platinum and ferricyanide/ferrocyanide, and the like. Separately, a reference electrode may be contacted with the medium 708 without disposing the reference electrode 707. In this case, the reference electrodes that can be used includes, in addition to a silver-silver chloride electrode, a standard hydrogen electrode, a saturated calomel electrode, a mercury-mercurous sulfate electrode and a mercurous oxide electrode, a reference electrode that uses as a standard potential an electrode reaction of a reversible redox system like ferrocene/ferrocenium ion, or ferricyanide/ferrocyanide. The measuring electrodes 706 that can be used include noble metals such as gold, silver, copper and platinum, the metals above modified with an alkanethiol single molecular film, and further electrodes modified with an ion-sensitive membrane, and the like. The mediums 708 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

As the hydrophilic surface, used are a surface treated with plasma, a surface coated with a single molecular film of a silane coupling agent or the like, a surface coated with an LB film, or the like. As the hydrophobic surface, used are a surface treated with fluorine oil or chlorofluorocarbon, a surface coated with a single molecular film of a silane coupling agent or the like, a surface coated with an LB film, or the like.

FIG. 8 is a diagram indicating another example of a measuring section of a small analyzer according to the present invention. The present measuring section includes two portions of upper and lower portions. FIG. 8(A) is a diagram of the lower portion not in use viewed from below; FIG. 8(A) is a sectional view of the lower portion not in use viewed from below; FIG. 8(C) is a diagram of the upper portion not in use viewed from below; FIG. 8(D) is a sectional view of the measuring section in use. The lower portion of the present measuring section includes a measuring container 801, a hydrophobic surface 802, a hydrophilic surface 803 and a substrate 804. The substrate 804 includes a plurality of pairs of field effect transistors 805 and measuring electrodes 806. The gate part of the field effect transistor 805 is connected to the measuring electrode 806 and the potential of the measuring electrode 806 can be measured by means of the field effect transistor 805. In addition, the substrate includes a reference electrode 807. The upper portion of the present measuring section includes a container lid 808, a hydrophobic surface 809 and a hydrophilic surface 810. Upon measurement, the lower portion is placed so as to be opposite to the upper portion; the sample solution 812 is placed so as to be sandwiched by the hydrophilic surfaces 803 and 810; the medium 811 is placed so as to be sandwiched by the hydrophobic surfaces 802 and 809. A reference electrode internal liquid 813 is placed on the reference electrode 807.

The procedure of measurement is in the following. First, the empty measuring container 801 is prepared and each of the sample solutions 812 is placed on each of the hydrophilic surfaces 803. Next, the container lid 808 is placed on the measuring container 801 and each of the sample solutions 812 is sandwiched by each of the hydrophilic surfaces 803 and 810. A spacer may be placed between the upper portion and the lower portion in order to specify the interval between the upper portion and the lower portion. In addition, a claw is disposed on the side of the upper portion and the claw may be hung on the upper portion to maintain the interval between the upper portion and the lower portion. Then, the medium 811 is poured into the container. At this time, attention is paid such that each of the sample solutions 812 is not moved from each of the hydrophilic surfaces 803 and 810. Additionally, attention is also paid such that air does not remain within the container. Then, a potential of each of the electrodes 806 is read out by means of each of the field effect transistors 805 as in another example. Although each of the field effect transistors 805 and each of the electrodes 806 are present in the lower portion in the present example, they may be present in the upper portion.

One example of the method of measuring a potential of the measuring electrode 806 by use of the field effect transistor 805 will be depicted. A voltage is applied to the reference electrode 807 in contact with the reference electrode internal liquid 813 from the power source separately provided. At this time, the power source may be a direct current source or an alternating current source. Next, voltage-current characteristics are measured between the source and the drain of the field effect transistor 805. A semiconductor parameter analyzer or its imitation circuit, or the like can be used for the measurement. The voltage-current characteristics measured are converted into a potential of the electrode 806 by use of voltage-current characteristics measured in advance.

The inside of the measuring container is divided into a hydrophilic surface and a hydrophobic surface, so that a sample solution can be arranged without a concave and a convex disposed within the measuring container. This makes it possible to improve the efficiency of cleaning. In addition, even if the specific gravity of a medium is larger than that of a sample solution, measurement can be carried out without the medium being not entered into the lower part of the sample solution if the absorbability of the sample solution onto the hydrophilic surface is larger than the buoyancy of the medium.

The sample solution 812 is sandwiched between the hydrophilic surfaces 803 of the measuring container 801 and the hydrophilic surfaces 810 of the container lid 808, whereby measurement can be carried out without a medium being not entered into the lower part of the sample solution even if the specific gravity of the medium is larger than that of the sample solution, since the absorbability of the sample solution onto the hydrophilic surface is larger than that of the case without the sandwiching. Additionally, since the sample solution is pushed down by the hydrophilic surface of the upper portion, even if a small amount of medium is entered into the lower part of the sample solution, measurement can be performed without any problems as long as the sample solution 812 is kept in contact with the electrode 810.

The combinations of the reference electrode 807 and the reference electrode internal liquid 813 that can be used include a silver-silver chloride electrode and an aqueous potassium chloride solution, a silver-silver chloride electrode and an aqueous sodium chloride solution, an electrode of a noble metal such as gold, silver, copper or platinum and ferrocene/ferrocenium ion, an electrode of a noble metal such as gold, silver, copper or platinum and ferricyanide/ferrocyanide, and the like. Separately, a reference electrode may be contacted with the medium 811 without disposing the reference electrode 807. In this case, the reference electrodes that can be used includes, in addition to a silver-silver chloride electrode, a standard hydrogen electrode, a saturated calomel electrode, a mercury-mercurous sulfate electrode and a mercurous oxide electrode, a reference electrode that uses as a standard potential an electrode reaction of a reversible redox system like ferrocene/ferrocenium ion, or ferricyanide/ferrocyanide. The measuring electrodes 806 that can be used include noble metals such as gold, silver, copper and platinum, the metals above modified with an alkanethiol single molecular film, and further electrodes modified with an ion-sensitive membrane, and the like. The mediums 811 that can be used include butanol, nitrobenzene, NPOE (2-nitrophenyl octyl ether), and the like. Organic salts that dissolve therein and can be used include tetrabutylammonium tetraphenylborate, and the like. In addition, usable organic salt simple substances include 1-ethyl-3-methylimidazolium bis(trifluoromethylsulfonyl)imide, 1-butyl-3-methylimidazolium bis(trifluoromethylsulfonyl)imide, 1-hexyl-3-methylimidazolium bis(trifluoromethylsulfonyl)imide, 1-methyl-3-octylimidazolium bis(trifluoromethylsulfonyl)imide, and the like.

As the hydrophilic surface, used are a surface treated with plasma, a surface coated with a single molecular film of a silane coupling agent or the like, a surface coated with an LB film, or the like. As the hydrophobic surface, used are a surface treated with fluorine oil or chlorofluorocarbon, a surface coated with a single molecular film of a silane coupling agent or the like, a surface coated with an LB film, or the like.

Figure 9:
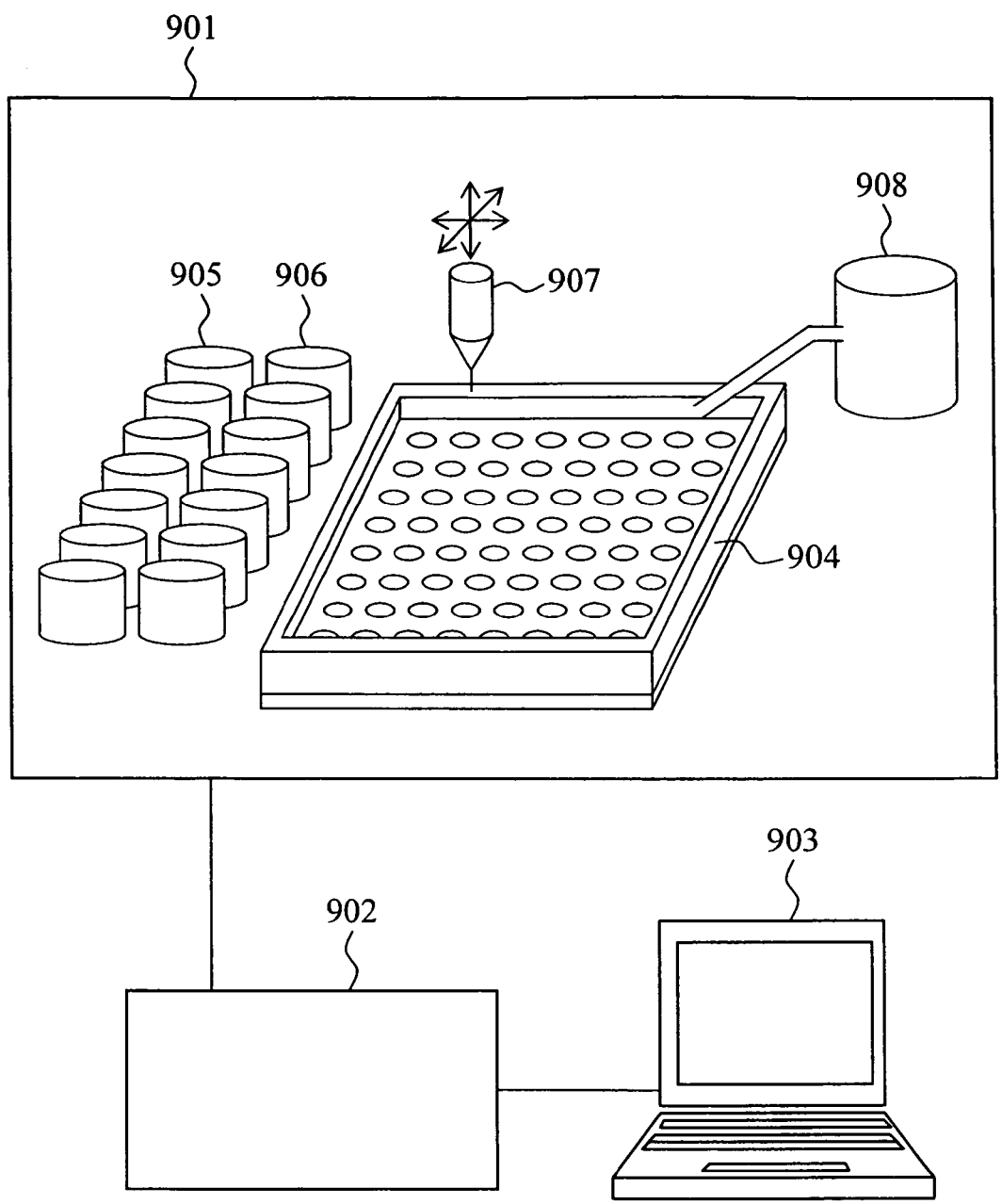
FIG. 9 is a block diagram indicating one example of an analyzer for analyzing a biological sample according to present invention.

FIG. 9 is a diagram indicating one example of a small analyzer according to the present invention. An analyzer of the present example includes a measuring section 901, a signal processing circuit 902, and a data processing device 903. The measuring section 901 includes a potential measuring part 904, a sample 905, a reagent 906, a dispenser 907 and a medium injecting part 908. For the potential measuring part 904, a measuring section as in examples of FIGS. 1 to 8 is used.

One example of the measuring procedure will be depicted. Each of the samples 905 is placed in a sample placing part (e.g., a vessel of a hydrophilic surface) of the potential measuring part 904 with use of the dispenser 907. Next, each of the reagents 906 is injected into each of the placed samples 905 with use of the dispenser 907. Then, a medium is injected into the potential measuring part 904 with use of the medium dispenser 908. Finally, the potential of each electrode of the potential measuring parts 904 is measured and a desired value is calculated by means of the signal processing circuit 902 and the data processing device 903.

Examples of the sample 905 include biological samples such as blood, serum, plasma and DNA. Examples of the reagent 906 include an enzyme reaction liquid, DNA, and the like. The sample 905 is mixed with the reagent 906 to thereby generate in an electrode a potential appropriate to a subject to be measured within the sample 905. For example, use of a material containing glucose of being a target to be measured as the sample 905 and a material containing potassium ferricyanide and glucose dehydrogenase as the reagent 906 leads to the reaction of the glucose with the potassium ferricyanide by the action of glucose dehydrogenase to generate gluconolactone and potassium ferricyanide. In the electrode, a potential according to the ratio between potassium ferricyanide and potassium ferrocyanide is generated, so the measurement of the potential of the electrode enables the concentration of glucose in the sample to be evaluated.

The measurement using the present measuring device renders it possible to make small the amount of the sample 905 and the reagent 906, needed for measurement. The reasons are, as described already in the other examples, that the potentiometry does not principally depend on a volume to be measured, that the measurement of the potential via a medium can be performed without causing a mixing of sample solutions and without a direct contact of the reference electrode with a sample solution, so the amount of a sample solution can be determined regardless of the size of the reference electrode, and that the presence of a medium makes a sample solution not directly contact with air, thereby the evaporation of the sample solution can be suppressed, and so forth.

Although the reagent 905 is mixed with the sample 906 in the potential measuring part 904 in the present example, materials mixed in another place may be injected into the potential measuring part 904. The dispenser 907 may be a single nozzle, a plurality of nozzles, a tube supplied from the sample 905 or the reagent 906. The dispenser 907 may use air pressure or a piezo element. What is needed is that the purpose of injection is achieved. Either the sample solution or the medium may be injected first, or the both may be injected at the same time.

Figure 10:
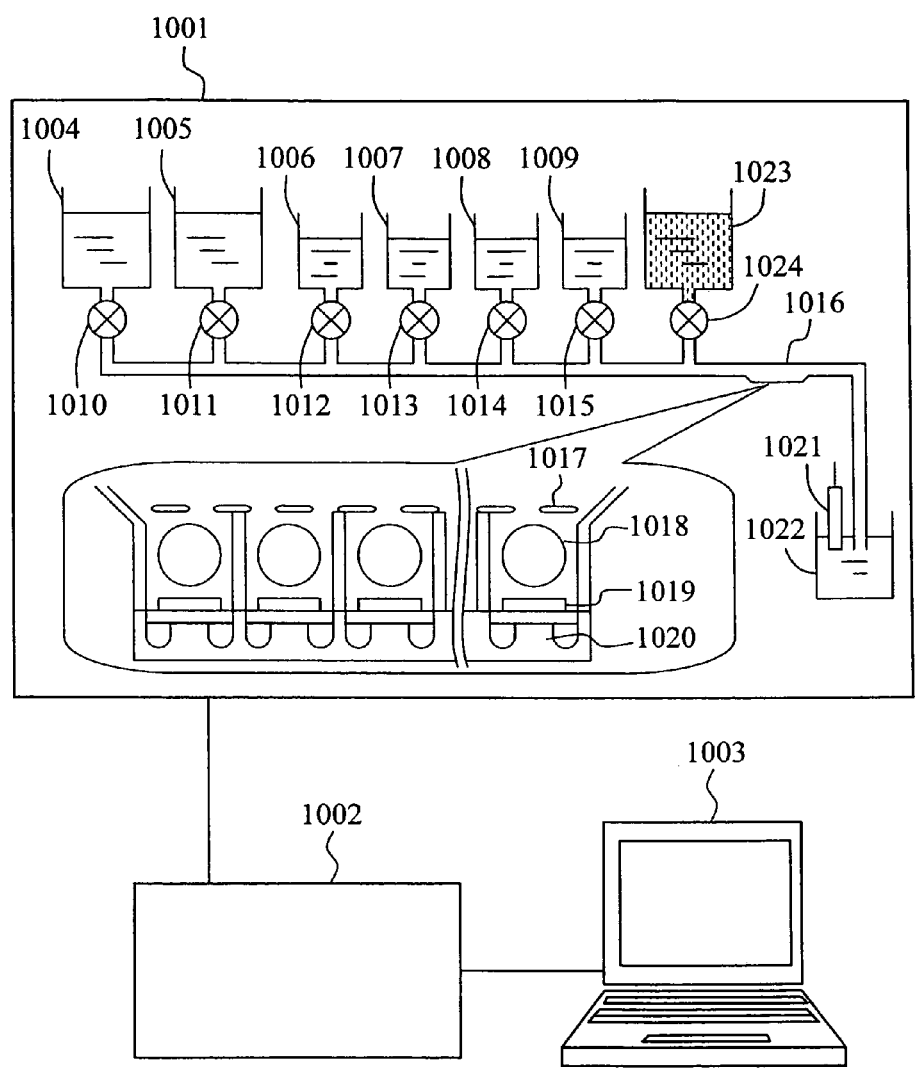
FIG. 10 is a block diagram indicating one example of an analyzer for analyzing a nucleic acid sequence according to present invention.

FIG. 10 is a diagram indicating one example of a small analyzer according to the present invention. An analyzer of the present example includes a measuring section 1001, a control and signal processing circuit 1002, and a data processing device 1003. The measuring section 1001 includes a cleaning solution container 1004, a reaction solution container 1005, a dATP solution container 1006, a dTTP solution container 1007, a dGTP solution container 1008, a dCTP solution container 1009, a medium container 1023, a cleaning solution supplying valve 1010, a reaction solution supplying valve 1011, a dATP solution supplying valve 1012, a dTTP solution supplying valve 1013, a dGTP solution supplying valve 1014, a dCTP solution supplying valve 1015, a medium supplying valve 1024, a measuring container 1016, a mesh 1017, a bead 1018, a measuring electrode 1019, a field effect transistor 1020, a reference electrode 1021 and a waste liquid container 1022. Opening or closing each valve enables the feed of each solution to a measuring cell to be controlled. Opening or closing each valve is performed according to an order determined by the control and signal processing circuit 1002.

The measuring container 1016 includes a plurality of vessels, and each vessel has placed therein one set each of the bead 1018, the measuring electrode 1019 and the field effect transistor 1020. To the surface of each bead 1018, probe DNA is fixed, and with the fixed probe DNA, target DNA is hybridized. A polystyrene bead, a magnetic bead, or the like is used for the bead. The surface of the bead is modified with a carboxyl group, an amino group, a maleimide group, a hydroxyl group, biotin, avidin, or the like. Here, probe DNA is immobilized that is modified with an amino group, a carboxyl group, an SH group, a silanol group, avidin, biotin, or the like. In place of a bead, a fine gold particle may be used. In this case, using probe DNA modified with an SH group or covering a fine gold particle with a molecule having a variety of functional groups makes it possible to immobilize probe DNA modified with a variety of functional groups. A bead is placed in each vessel and then the mesh 1017 is placed such that the bead does not spring out of the vessel during solution exchange. To the surface of the measuring electrode 1019, an electrochemically active substance may be fixed via an insulating molecule. For example, when gold is used for the measuring electrode 1019, 11-aminoundecathiol is fixed to the electrode surface as an insulating molecule and further pyrroloquinoline quinone (PQQ) serving as an electrochemically active substance is immobilized therewith through the use of an amide bond produced by the dehydration reaction of an amino group with a carboxyl group. An electrode of a noble metal such as a gold electrode or a carbon electrode is used for the measuring electrode 1019. Instead of a measuring electrode, a material that generates a potential appropriate to the concentration of a subject to be measured such as a sensitive membrane may be employed. The reference electrode 1021 is in contact with a solution within the waste liquid container 1022.

Reduced nicotinamide adenine dinucleotide (NADH) was used as a cleaning solution container 1004. As a reaction solution within the reaction solution container 1005, used was a solution prepared by dissolving DNA polymerase, pyruvate orthophosphate dikinase (PPDK), lactate dehydrogenase, phosphoenolpyruvate (PEP), adenosine monophosphate (AMP) and NADH in a tris-HCl buffer solution. For solutions in the dATP solution container 1006, the dTTP solution container 1007, the dGTP solution container 1008 and the dCTP solution container 1009, used was solutions prepared by dissolving dATP, dTTP, dGTP and dCTP in a tris-HCl buffer solution, respectively. Although a silver-silver chloride reference electrode using a saturated potassium chloride solution for its internal liquid was used in the reference electrode 1021, any reference electrode may be used so long as its variation of the potential is sufficiently small as compared with the potential change during one-base elongation. Although the reference electrode 1021 is made contact with a solution within the waste liquid container 1022 in the present example, the reference electrode 1021 may be placed in any place in the measuring system so long as it is in contact with the solution within the measuring cell. As for a bead, a polyethylene bead with a diameter of 50 µm having a carboxyl terminal was used. For immobilization of primer DNA to a bead, beads were mixed with primer DNA modified with an amino group and then N-hydroxysuccinimide (NHS) and 1-ethyl-3-(3-dimethylaminopropyl)carbodiimide (EDC) were added thereto to thereby chemically bind the primer DNA to the bead. A gold electrode was used for the measuring electrode 1019. 11-Amino-1-undecanethiol (11-AUT) was used as an insulating molecule, and PQQ as an electrochemically active substance. A 11-AUT solution was used to form a single molecular film of 11-AUT on the surface of the gold electrode. To this electrode surface, added dropwise was a mixture solution of PQQ (pyrroloquinoline quinone), Sulfo-NHS (N-hydroxysulfosuccinimide) and EDC, and the resultant material was reacted overnight and then PQQ was immobilized by means of the chemical bonding of an amino group of 11-AUT with a carboxyl group of PQQ.

Figure 11:
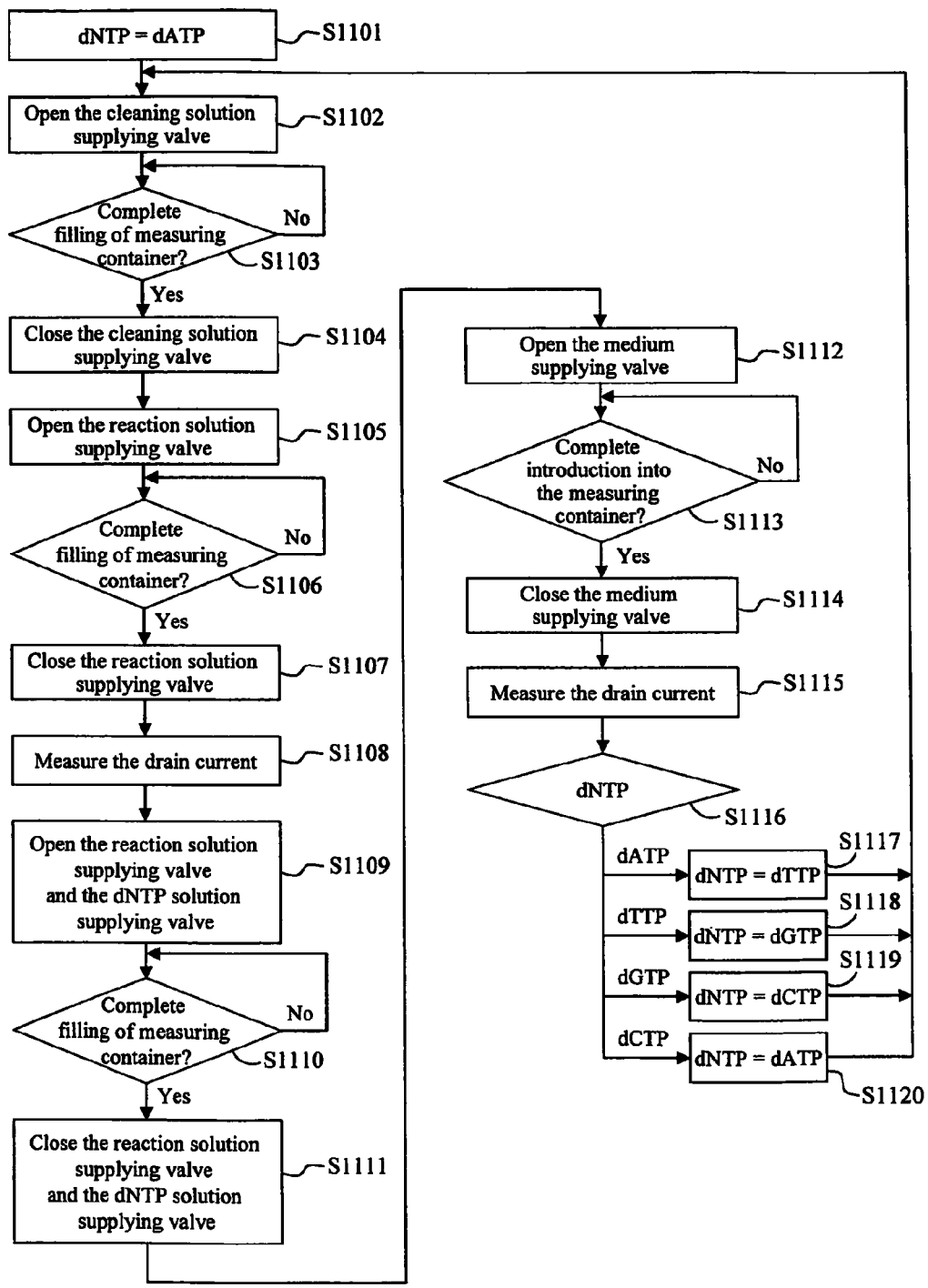
FIG. 11 is a diagram indicating one example of a measuring flow by an analyzer for analyzing a nucleic acid sequence according to present invention.

One example of the measuring procedure is indicated in FIG. 11. Firstly, the cleaning solution supplying valve 1010 was opened (S1102) and the inside of a measuring container was filled with a cleaning solution (S1103) and then the cleaning solution supplying valve 1010 was closed (S1104). This operation rendered in a reduction state an electrochemically active substance immobilized to the surface of the measuring electrode 1019. Next, the reaction solution supplying valve 1011 was opened (S1105) and the inside of the measuring container 1016 was filled with a reaction solution (S1106) and then the reaction solution supplying valve 1011 was closed (S1107). A constant voltage $V_G$ was applied to the reference electrode 1021 and then the drain current of each of the field effect transistors was measured (S1108). Each drain current value at this time was set to be $I_D(1, n)$ (n refers to a number assigned to a field effect transistor). The reaction solution supplying valve 1011 and the dNTP solution supplying valve 1012, 1013, 1014 or 1015 were opened (S1109) and the inside of the measuring container 1016 was filled with a mixture solution of the reaction solution and a dNTP solution (S1110) and then the reaction solution supplying valve 1011 and the dNTP solution supplying valve 1012, 1013, 1014 or 1015 were closed (S1111). Immediately, the medium supplying valve 1024 was opened (S1112) and a medium was introduced into the measuring container 1016 (S1113) and then the medium supplying valve 1024 was closed (S1114).

Figure 12A:
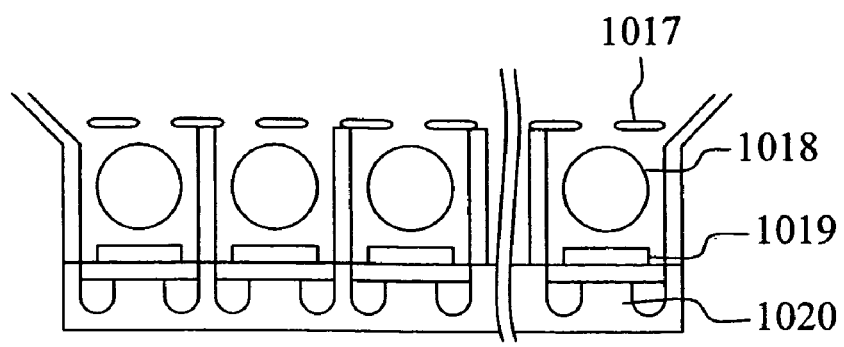
FIG. 12 is a diagram indicating one example of medium introduction by an analyzer for analyzing a nucleic acid sequence according to present invention.
Figure 12B:
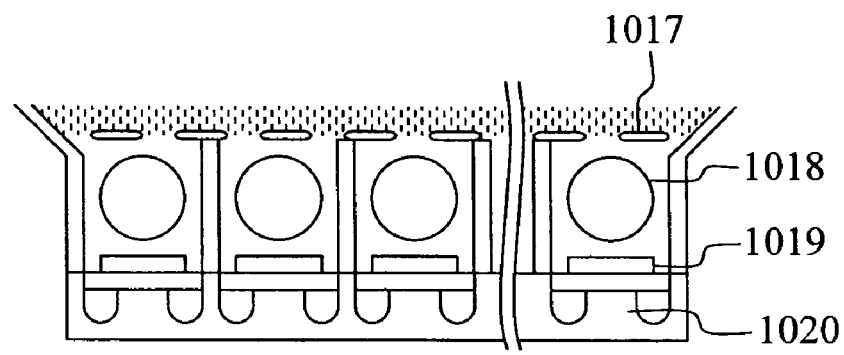

This operation changed a state before medium introduction (FIG. 12(A)) into a state after medium introduction (FIG. 12(B)). At this time, the medium was not intruded into each vessel and a liquid within each vessel remained separate. The constant voltage $V_G$ was applied to the reference electrode 1021 and then the drain current of each of the field effect transistors 1020 was measured (S1115). Each drain current value at this time was set to be $I_D(2, n)$ (n is a number of a measuring cell), with $\Delta I_D(n) = I_D(2, n) - I_D(1, n)$. $\Delta I_D$ is a change in drain current occurring with dNTP supply in each field effect transistor. Again, the operation was returned to opening of the cleaning solution supplying valve 1010 (S1102) and dATP, dTTP, dGTP or dCTP in the order listed was used as dNTP and measurement was repeated (S1101, S1116 to S1120).

A solution prepared by dissolving dATP in a reaction solution within the reaction solution container 1005 in advance can also be used as a dATP solution within the dATP solution container 1006; a solution prepared by dissolving dTTP in a reaction solution within the reaction solution container 1007 in advance can also be used as a dTTP solution within the dTTP solution container 1007; a solution prepared by dissolving dGTP in a reaction solution within the reaction solution container 1005 in advance can also be used as a dGTP solution within the dGTP solution container 1008; a solution prepared by dissolving dCTP in a reaction solution within the reaction solution container 1005 in advance can also be used as a dCTP solution within the dCTP solution container 1009. In this case, an operation in which the reaction solution supplying valve 1011 and the dNTP solution supplying valve 1012, 1013, 1014 or 1015 are opened (S1109) is changed into an operation in which the dNTP solution supplying valve 1012, 1013, 1014 or 1015 is opened. The order of dATP, dTTP, dCTP or dGTP using as dNTP may be arbitrary so long as the operation has a four-time period. Instead of dNTP, a material such as an analogue in which a part of its molecules are substituted by sulfur atoms (dNTPαS, sulfur substitution at 4' position of sugar moiety (N. Inoue et. al., Nucleic Acids Research, 3476-3483, 34, 2006)) can be used as long as it is base-sequence specifically incorporated into synthetic reaction of double-stranded DNA by a DNA chain synthesis enzyme to generate pyrophosphoric acid.

A cleaning solution is used for initialization of the surface potential of an electrode changed by transformation of pyrophosphoric acid into a redox state of a redox substance. In the present example, although the surface potential is increased by elongation, the surface potential is decreased by reduction substance within a cleaning solution, whereby elongation can be measured again. For the cleaning solution, a solution containing a reduction substance such as a thiol compound can also be used in addition to the above mentioned substances. In addition, depending on the combination of a redox substance and an enzyme within a reaction solution, elongation may decrease the surface potential. In this case, as a cleaning solution, a solution containing an oxidizing substance such as aqueous hydrogen peroxide and potassium ferrocyanide can also be employed. Primer DNA may also be immobilized to each vessel of the measuring cell 1016, or to the measuring electrode 1019. Instead of immobilization of primer DNA, sample DNA may be immobilized and to the immobilized sample DNA may also be hybridized primer DNA. Sample DNA may also be hybridized to primer DNA and then immobilized.

Separation of a reaction solution within each vessel by use of a liquid immiscible with water for a medium makes it possible to prevent reaction solutions from mixing with each other. For the case of nonuse of a medium, diffusion of a solution within each vessel to the outside of the vessel mixes the solution with a solution in an adjacent vessel and generates an error signal in an electrode within the adjacent vessel. Although replacement of a part of a medium by air can prevent the reaction solutions from mixing with each other, a constitution in FIG. 10 does not transmit a potential from the reference electrode to a reaction solution, and thus a surface potential cannot be precisely measured. As another means for solving this problem, disposition of a small reference electrode within a vessel is considered. However, it is difficult to obtain durability and stability and, in the first place, it is very difficult to construct a reference electrode in a site having a size of about 100 μm or less. Application of a voltage from a reference electrode to each vessel via a medium as in the present example can prevent the reaction solutions from mixing with each other even by use of a conventional reference electrode.

Figure 13A:
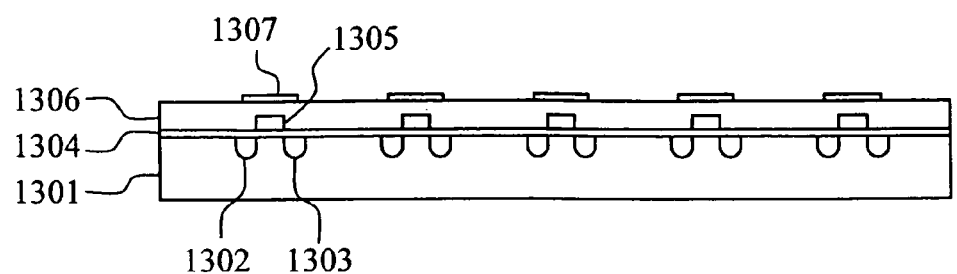
FIG. 13 is a diagram indicating one example of a substrate used by an analyzer for analyzing a small amount of liquid according to present invention.
Figure 13B:
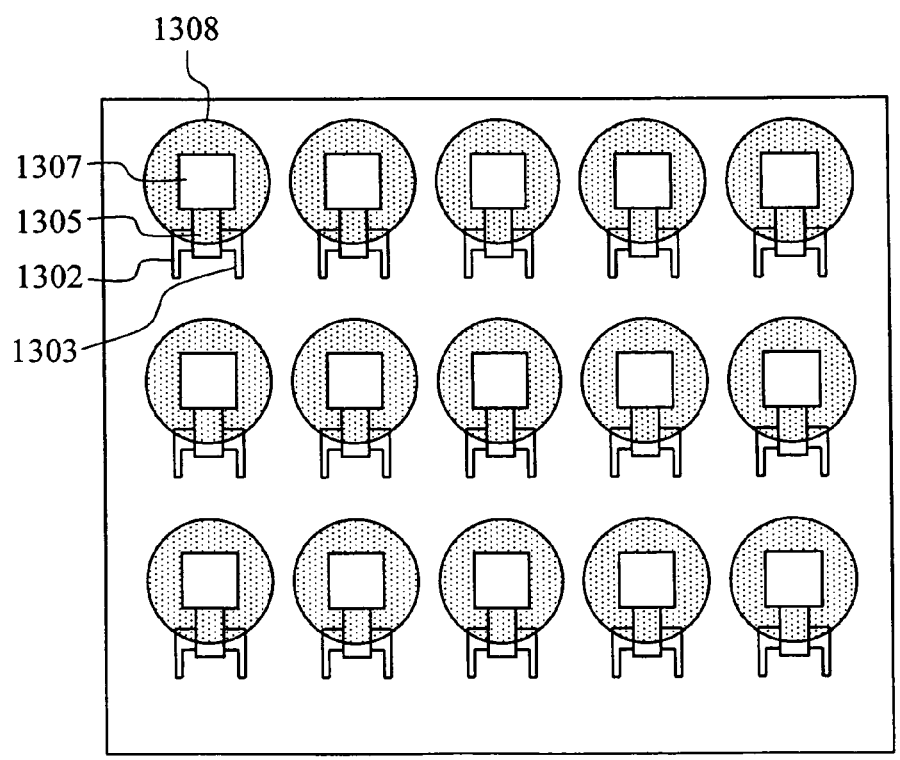

FIG. 13 is a diagram indicating one example of a field effect transistor and a substrate having an electrode used in another example of the present invention. FIGS. 13(A) and 13(B) illustrate, respectively, a cross section structure and a planar structure. A field effect transistor forms a source 1302, a drain 1303 and a gate insulating film 1304 on the surface of a silicon substrate 1301, and a gate part is communicated with an electrode 1307 via electric conductive wiring 1305. The surface of the substrate is covered with a nitride film 1306 except the electrode 1307. Around the electrode 1307 is a plasma-treated hydrophilic surface 1308.

FIG. 14 is a diagram indicating results obtained by measurement of three different samples by means of a small analyzer according to the present invention. The apparatus of FIG. 1 was used for the measurement. Each vessel had a diameter of 2 mm and a depth of 3.5 mm. As the medium 105, used was 50 μl of 1-ethyl-3-methylimidazolium (trifluoromethylsulfonyl)imide. As the sample solutions 106, used were three kinds of 9 μl solutions of combination of PBS (10 mM $Na_2HPO_4$, 1.8 mM $KH_2PO_4$, 137 mM NaCl, 2.7 mM KCl, pH 7.4) and potassium ferricyanide/potassium ferrocyanide solutions (respectively, 1:9, 5:5, 9:1) prepared by dissolving the substances in the ratios below.

Figure 14A:
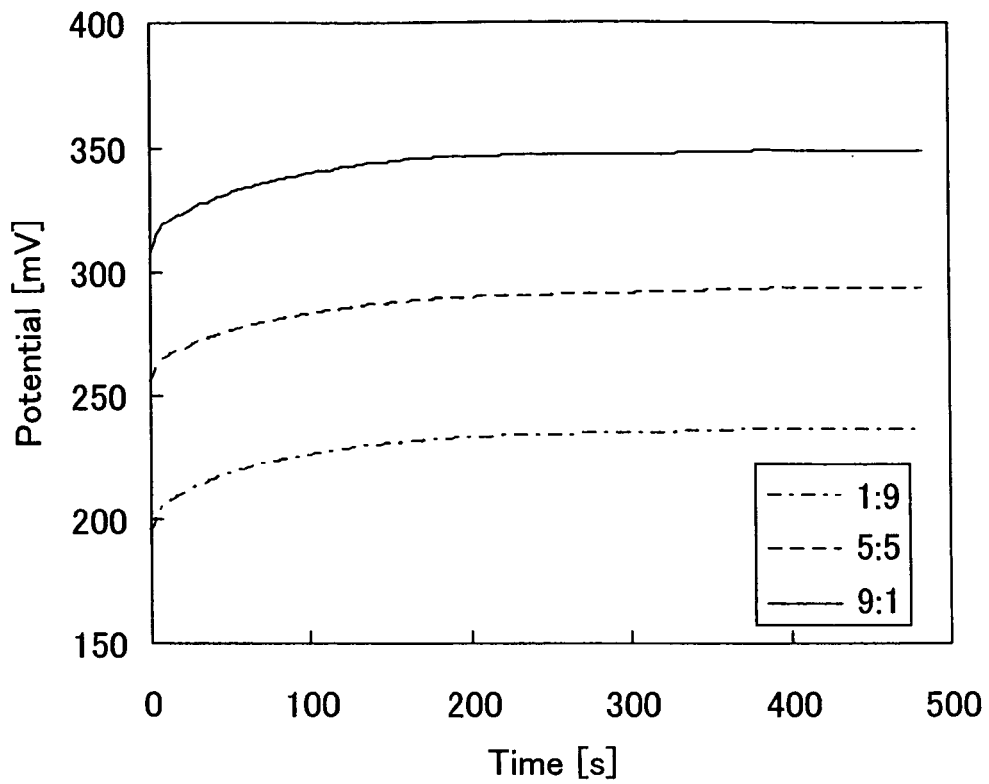
FIG. 14 is a diagram indicating one example of measurement results using an analyzer for analyzing a small amount of liquid according to present invention.
Figure 14B:
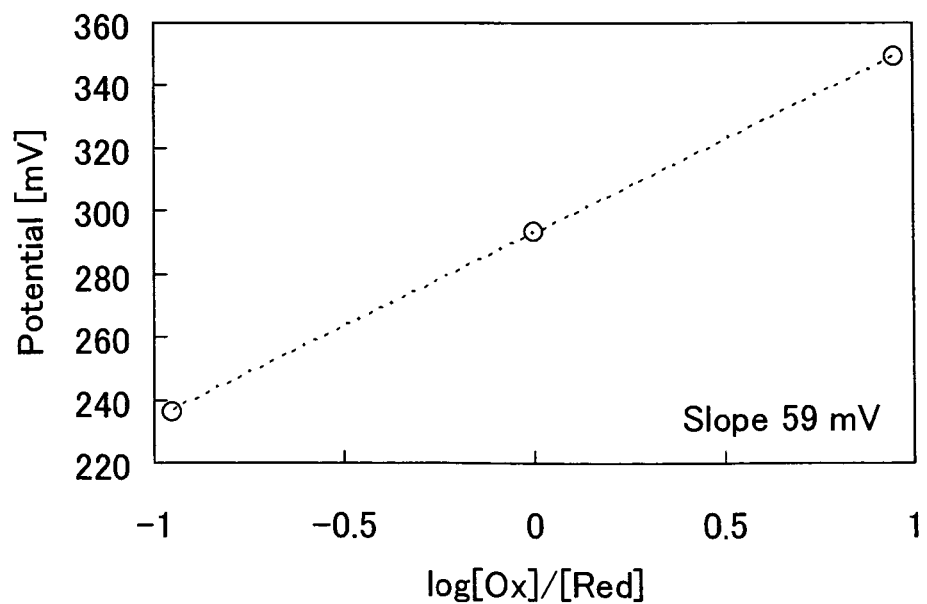

1:9 10 mM potassium ferricyanide, 90 mM potassium ferrocyanide
5:5 50 mM potassium ferricyanide, 50 mM potassium ferrocyanide
9:1 90 mM potassium ferricyanide, 10 mM potassium ferrocyanide Gold was used for the electrode 107 and a silver-silver chloride reference electrode having a saturated potassium chloride solution as an internal liquid was used for the reference electrode 109. The measuring temperature was 24° C. FIG. 14(A) indicates the potential change from moment to moment after measurement initiation. Although a drift of a potential is seen till 200 seconds or above after measurement initiation, the potential differences in the cases of the ratios 1:9, 5:5 and 9:1 are kept almost constant. FIG. 14(B) indicates that the potential after the measurement completion is plotted against log [Ox]/[Red] (abscissa), where [Ox] represents the concentration of potassium ferricyanide of being an oxidizing substance, and [Red] represents the concentration of potassium ferrocyanide of being a reducing substance. According to the Nernst equation, a potential proportional to log [Ox]/[Red] is generated in the electrode and its slope is 59 mV at 25° C. In the experiment, a slope of 59 mV equal to the theoretical value was observed.

FIG. 15 is a diagram indicating results obtained by measurement of three different samples by means of a small analyzer according to the present invention. The apparatus of FIG. 1 was used for the measurement. Each vessel had a diameter of 2 mm and a depth of 3.5 mm. As the medium 105, used was 50 μl of nitrophenyl octyl ether containing 10 mg/ml tetrabutylammonium tetraphenylborate. As the sample solutions 106, used were three kinds of 9 μl solutions of combination of PBS (10 mM $Na_2HPO_4$, 1.8 mM $KH_2PO_4$, 137 mM NaCl, 2.7 mM KCl, pH 7.4) and potassium ferricyanide/ potassium ferrocyanide solutions (respectively, 1:9, 5:5, 9:1) prepared by dissolving the substances in the ratios below.

1:9 10 mM potassium ferricyanide, 90 mM potassium ferrocyanide

5:5 50 mM potassium ferricyanide, 50 mM potassium ferrocyanide

9:1 90 mM potassium ferricyanide, 10 mM potassium ferrocyanide

Figure 15A:
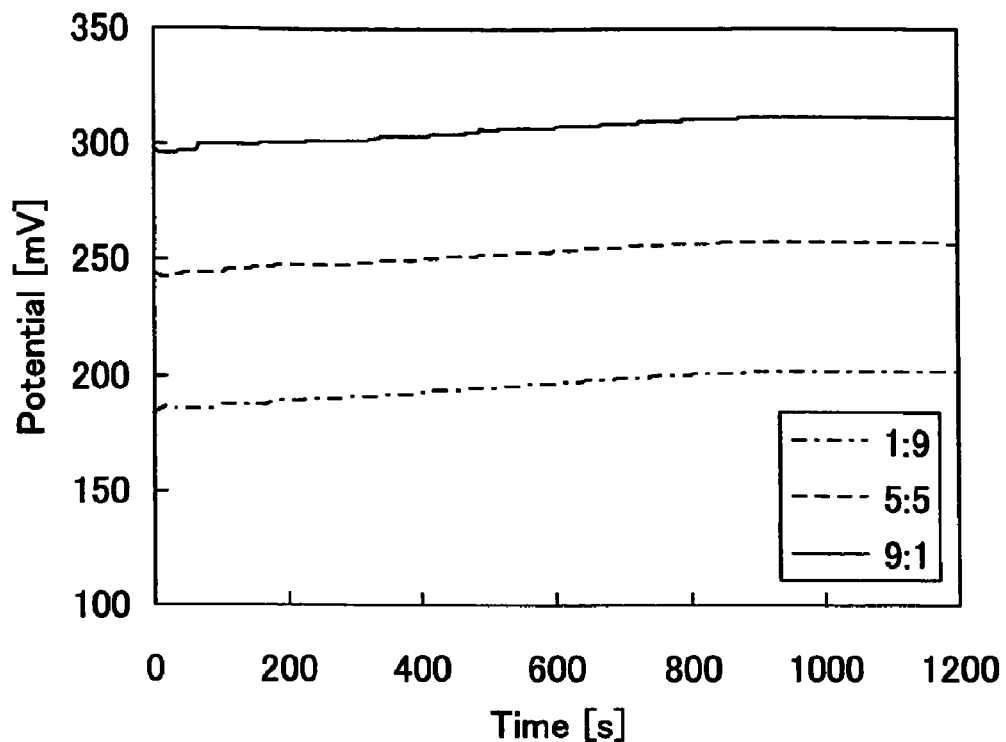
FIG. 15 is a diagram indicating one example of measurement results using an analyzer for analyzing a small amount of liquid according to present invention.
Figure 15B:
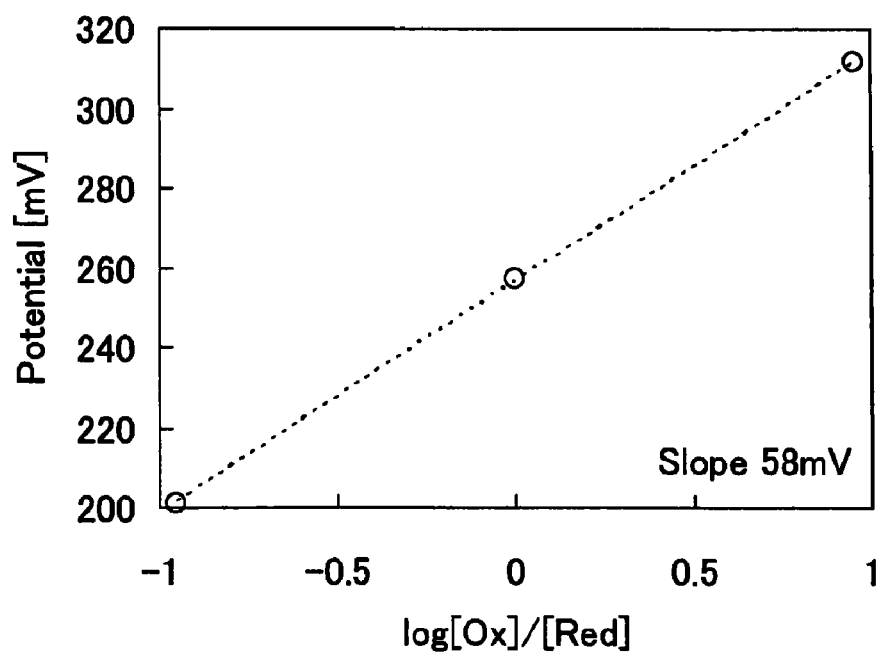

Gold was used for the electrode 107 and a silver-silver chloride reference electrode having a saturated potassium chloride solution as an internal liquid was used for the reference electrode 109. The measuring temperature was 24° C. FIG. 15(A) indicates the potential change from moment to moment after measurement initiation. Although the drift of a potential is seen till 800 seconds or above after measurement initiation, the potential differences in the cases of the ratios 1:9, 5:5 and 9:1 are kept almost constant. FIG. 15(B) indicates that the potential after the measurement completion is plotted against log [Ox]/[Red] (abscissa), where [Ox] represents the concentration of potassium ferricyanide of being an oxidizing substance, and [Red] represents the concentration of potassium ferrocyanide of being a reducing substance. According to the Nernst equation, a potential proportional to log [Ox]/[Red] is generated in the electrode and its slope is 59 mV at 25° C. In the experiment, a slope of 58 mV almost equal to the theoretical value was observed.

EXPLANATION OF REFERENCE NUMERALS 101, 201, 501, 601, 901, 1001 . . . MEASURING SECTION
102, 202, 502, 602, 902, 1002 . . . SIGNAL PROCESSING CIRCUIT
103, 203, 503, 603, 903, 1003 . . . DATA PROCESSING DEVICE
104, 204, 301, 401, 504, 604, 701, 1016 . . . MEASURING CONTAINER
105, 205, 305, 408, 505, 605, 708, 811 . . . MEDIUM
106, 206, 306, 409, 506, 606, 709, 801, 812 . . . SAMPLE SOLUTION
107, 304, 404, 511, 611, 706, 806, 1019, 1307 . . . ELECTRODE
108, 208 . . . VOLTMETER
109, 210, 508, 612, 707, 807, 1021 . . . REFERENCE ELECTRODE
207 . . . MEASURING ELECTRODE
209, 608, 710, 813 . . . REFERENCE ELECTRODE INTERNAL LIQUID
302, 402, 406, 702, 802, 809 . . . HYDROPHOBIC SURFACE
303, 403, 407, 703, 803, 810, 1308 . . . HYDROPHILIC SURFACE
405, 808 . . . CONTAINER LID
507, 607, 704, 804 . . . SUBSTRATE
509, 609 . . . POWER SOURCE
510, 610, 705, 805, 1020 . . . FIELD EFFECT TRANSISTOR
904 . . . POTENTIAL MEASURING PART
905 . . . SAMPLE
906 . . . REAGENT
907 . . . DISPENSER
908 . . . MEDIUM INJECTING PART
1004 . . . CLEANING SOLUTION CONTAINER
1005 . . . REACTION SOLUTION CONTAINER
1006 . . . dATP SOLUTION CONTAINER
1007 . . . dTTP SOLUTION CONTAINER
1008 . . . dGTP SOLUTION CONTAINER
1009 . . . dCTP SOLUTION CONTAINER
1010 . . . CLEANING SOLUTION SUPPLYING VALVE
1011 . . . REACTION SOLUTION SUPPLYING VALVE
1012 . . . dATP SOLUTION SUPPLYING VALVE
1013 . . . dTTP SOLUTION SUPPLYING VALVE
1014 . . . dGTP SOLUTION SUPPLYING VALVE
1015 . . . dCTP SOLUTION SUPPLYING VALVE
1017 . . . MESH
1018 . . . BEAD
1022 . . . WASTE LIQUID CONTAINER
1023 . . . MEDIUM CONTAINER
1024 . . . MEDIUM SUPPLYING VALVE
1301 . . . SILICON SUBSTRATE
1302 . . . SOURCE
1303 . . . DRAIN
1304 . . . GATE INSULATING FILM
1305 . . . ELECTRIC CONDUCTIVE WIRING
1306 . . . NITRIDE FILM

What is claimed is:

1. An analyzer comprising:
a container provided with a plurality of sample placing parts;
a plurality of measuring electrodes respectively placed in the plurality of the sample placing parts;
a medium in contact with a plurality of water-soluble sample solutions respectively placed in the plurality of the sample placing parts thereby limiting mixing of the plurality of water-soluble sample solutions with each other,
the medium being a liquid containing an organic salt and being immiscible with water or a liquid organic salt immiscible with water;
one reference electrode provided with an internal liquid accommodating part accommodating an internal liquid and arranged so as to make contact with the medium; and
a means for measuring a potential difference between each of the plurality of the measuring electrodes and the reference electrode.

2. The analyzer according to claim 1, wherein
the measuring electrode is any one of a noble metal, carbon and an ion-sensitive membrane.

3. The analyzer according to claim 1, wherein
the volume of the internal liquid accommodating part is larger than the volume of a sample solution placed in the sample placing part.

4. The analyzer according to claim 1, wherein
the means for measuring the potential difference includes a field effect transistor.

5. The analyzer according to claim 1, comprising:
a medium introducing part from which the medium is introduced into the container.

6. The analyzer according to claim 1, wherein
the plurality of the sample placing parts are all partitioned by partitioning walls.

7. The analyzer according to claim 6, wherein the medium forms a continuous cover over each of the plurality of sample placing parts, thereby completely separating each of the plurality of sample placing parts from each other.

8. The analyzer according to claim 1, wherein:
the container has a plurality of hydrophilic regions independently disposed on the bottom thereof, the hydrophilic regions serving as the plurality of the sample placing parts, wherein
a region between the plurality of the hydrophilic regions is hydrophobic.

9. The analyzer according to claim 1, wherein
the potential difference measured by the means for measuring the potential difference is a potential difference between each of the measuring electrodes and the reference electrode across the interface between the measuring electrode and the sample solution, the interface between the sample solution and the medium, and the interface between the medium and the internal liquid.

10. The analyzer according to claim 1, wherein the specific gravity of the medium is greater than that of the solution.

11. The analyzer according to claim 1, wherein the medium suppresses a deviation in measurable electric potential among the plurality of water-soluble sample solutions.

12. An analyzer comprising:
a container provided with a plurality of sample placing parts and one reference electrode placing part,
a plurality of measuring electrodes respectively arranged in the plurality of the sample placing parts;
a reference electrode placed in the reference electrode placing part;
a reference electrode internal liquid placed so as to make contact with the reference electrode;
a plurality of water-soluble sample solutions respectively arranged in the plurality of the sample placing parts and the reference electrode internal liquid;
a medium in contact with all of the plurality of water-soluble sample solutions,
the medium being a liquid containing an organic salt and being immiscible with water, or a liquid organic salt immiscible with water; and
a means for measuring a potential difference between each of the plurality of the measuring electrodes and the reference electrode.

13. The analyzer according to claim 12, wherein
the measuring electrode is a noble metal, carbon or an ion-sensitive membrane.

14. The analyzer according to claim 12, wherein
the means for measuring the potential difference includes a field effect transistor.

15. The analyzer according to claim 12, comprising:
a medium introducing part which introduces the medium into the container.

16. The analyzer according to claim 12, wherein
the plurality of the sample placing parts and one reference electrode placing part are all partitioned by partitioning walk.

17. The analyzer according to claim 12, comprising:
the container has a plurality of hydrophilic regions independently disposed on the bottom thereof, the hydrophilic regions serving as the plurality of the sample placing parts and one reference electrode placing part, wherein
a region between the plurality of the hydrophilic regions is hydrophobic.

18. The analyzer according to claim 12, wherein
the potential difference measured by the means for measuring the potential difference is a potential difference between each of the measuring electrodes and the reference electrode across the interface between the measuring electrode and the sample solution, the interface between the sample solution and the medium, and the interface between the medium and the reference electrode internal liquid.

19. An analyzer comprising:
a container having a plurality of reaction vessels all partitioned by partitioning walls, the reaction vessels each having nucleic acid immobilized therein or each having a member arranged therein with nucleic acid immobilized therein;
a plurality of measuring electrodes respectively arranged in the plurality of the reaction vessels;
one reference electrode which includes an internal liquid accommodating part accommodating an internal liquid, and which is placed so as to make contact with a solution introduced into the container;
a measuring section including a plurality of field effect transistors measuring a potential difference between each of the plurality of the measuring electrodes and the reference electrode;
a first supplying part of supplying dATP or its analogue to the container;
a second supplying part of supplying dGTP or its analogue to the container;
a third supplying part of supplying dCTP or its analogue to the container;
a forth supplying part of supplying dTTP or its analogue to the container;
a fifth supplying part of supplying a water-soluble reaction solution to the container;
a sixth supplying part of supplying a cleaning solution to the container;
a seventh supplying part which supplies to the container a liquid containing an organic salt and being immiscible with water, or a medium including a liquid organic salt immiscible with water; and
a controlling section which controls the supply of solutions to the container from the first supplying part, the second supplying part, the third supplying part, the fourth supplying part, the fifth supplying part, the sixth supplying part and the seventh supplying part, and causes the measuring section to measure the potential difference synchronously with the supply of a reaction solution from the fifth supplying part and the supply of a medium from the seventh supplying part.

20. The analyzer according to claim 19, wherein the controlling section controls (i) the supply of the fifth solution into the plurality of reaction vessels and (ii) the supply of the solution to the seventh supplying part which thereby allows the seventh solution to completely cover all of the fifth solution in all of the reaction vessels.

* * * * *